(12) United States Patent
Lang et al.

(10) Patent No.: US 11,883,599 B2
(45) Date of Patent: Jan. 30, 2024

(54) PATIENT INTERFACE COMPONENT

(71) Applicant: ResMed Pty Ltd, Bella Vista (AU)

(72) Inventors: Bernd Christoph Lang, Graefelfing (DE); Andreas Kirchberger, Miesbach (DE); Johannes Nickol, Neukenroth (DE); Jens Rothfuss, Unterschleissheim (DE); Johann Sebastian Burz, Germaringen (DE); Robert Eibl, Bad Toelz (DE); Christian Bayer, Penzberg (DE); Anne Claude Andrée Armelle Reiser, Munich (DE)

(73) Assignee: ResMed Pty Ltd, Bella Vista (AU)

( * ) Notice: Subject to any disclaimer, the term of this patent is extended or adjusted under 35 U.S.C. 154(b) by 507 days.

(21) Appl. No.: 17/194,429

(22) Filed: Mar. 8, 2021

(65) Prior Publication Data

US 2021/0252242 A1    Aug. 19, 2021

Related U.S. Application Data

(63) Continuation of application No. 15/274,438, filed on Sep. 23, 2016, now Pat. No. 10,967,144.

(30) Foreign Application Priority Data

Sep. 25, 2015    (EP) .................................. 15186945

(51) Int. Cl.
*A61M 16/06* (2006.01)
*A61M 15/08* (2006.01)
(Continued)

(52) U.S. Cl.
CPC ........ *A61M 16/0622* (2014.02); *A61M 15/08* (2013.01); *A61M 16/06* (2013.01);
(Continued)

(58) Field of Classification Search
CPC .. A61F 2013/00646; A61F 2013/00285; A61F 5/56; A61F 2013/00314;
(Continued)

(56) References Cited

U.S. PATENT DOCUMENTS 4,782,832 A    11/1988 Trimble et al.
4,944,310 A     7/1990 Sullivan
(Continued)

FOREIGN PATENT DOCUMENTS

WO    WO 98/004310 A1    2/1998
WO    WO 98/034665 A1    8/1998
(Continued)

OTHER PUBLICATIONS

Hashimoto et al., Permeability of adhesive resin films Jun. 22, 2005 Wiley Periodicals, Inc. J Biomed Mater Res Part B: Appl Biomater 74B: 699-705 (Year: 2005).*
(Continued)

*Primary Examiner* — Elliot S Ruddie
(74) *Attorney, Agent, or Firm* — Nixon & Vanderhye P.C.

(57) ABSTRACT

The present technology relates to a pad for forming a seal forming structure against a user's skin for use with a patient interface, the pad comprising, a base layer, a fibre layer comprising a plurality of fibers for contacting a patient's skin, and a connection layer for connecting the fibers to the base material, wherein the base layer and/or the fibre layer is/are adapted to act as a reservoir for substances. Furthermore, it relates to a set of pads, a kit and a patient interface.

25 Claims, 9 Drawing Sheets

(51) Int. Cl.
*A61M 16/22* (2006.01)
*B32B 5/02* (2006.01)
*B32B 5/18* (2006.01)
*B32B 5/24* (2006.01)
*B32B 7/12* (2006.01)
*B32B 9/02* (2006.01)
*B32B 25/10* (2006.01)
*B32B 25/20* (2006.01)

(52) U.S. Cl.
CPC .... *A61M 16/0605* (2014.02); *A61M 16/0666* (2013.01); *A61M 16/22* (2013.01); *B32B 5/02* (2013.01); *B32B 5/18* (2013.01); *B32B 5/245* (2013.01); *B32B 7/12* (2013.01); *B32B 9/02* (2013.01); *B32B 25/10* (2013.01); *B32B 25/20* (2013.01); *A61M 16/0633* (2014.02); *B32B 2266/0207* (2013.01); *B32B 2266/06* (2013.01); *B32B 2535/00* (2013.01)

(58) Field of Classification Search
CPC ........ A61M 15/08; A61M 16/06–0694; A61M 16/22; A61M 16/0633; B32B 5/02; B32B 5/18; B32B 5/245; B32B 7/12; B32B 9/02; B32B 25/10; B32B 25/20; B32B 2266/0207; B32B 2266/06; B32B 2535/00
See application file for complete search history.

(56) References Cited

U.S. PATENT DOCUMENTS

| | | | |
|---|---|---|---|
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 2004/0118400 | A1 | 6/2004 | Chou |
| 2008/0289633 | A1 | 11/2008 | Kwok et al. |
| 2009/0044808 | A1 | 2/2009 | Guney et al. |
| 2009/0050156 | A1 | 2/2009 | Ng et al. |
| 2010/0000534 | A1 | 1/2010 | Kooij et al. |
| 2011/0209701 | A1* | 9/2011 | Derringer ......... A61M 16/0605 128/206.25 |
| 2014/0251338 | A1 | 9/2014 | Asvadi et al. |
| 2016/0001029 | A1* | 1/2016 | Bayer ................ A61M 16/0611 128/206.24 |
| 2017/0087322 | A1 | 3/2017 | Lang et al. |

FOREIGN PATENT DOCUMENTS

| | | | | |
|---|---|---|---|---|
| WO | WO 2000/078381 | A1 | 12/2000 | |
| WO | WO 2004/073778 | A1 | 9/2004 | |
| WO | WO 2005/063328 | A1 | 7/2005 | |
| WO | WO 2006/074513 | A1 | 7/2006 | |
| WO | WO 2006/130903 | A1 | 12/2006 | |
| WO | WO-2007135424 | A1 * | 11/2007 | ............. A01N 25/34 |
| WO | WO 2009/052560 | A1 | 4/2009 | |
| WO | WO 2010/135785 | A1 | 12/2010 | |
| WO | WO 2012/131001 | A2 | 10/2012 | |
| WO | WO 2012/171072 | A1 | 12/2012 | |
| WO | WO 2013/020167 | A1 | 2/2013 | |

OTHER PUBLICATIONS

"*Respiratory Physiology*", by John B. West, Lippincott Williams & Wilkins, 9th edition published 2012 (8 pages).

Extended European Search Report dated Mar. 4, 2016 in European Application No. 15186945.0 (8 pages).

Communication Pursuant to Article 94(3) EPC dated Sep. 12, 2018 in European Application No. 15186945.0 (7 pages).

* cited by examiner

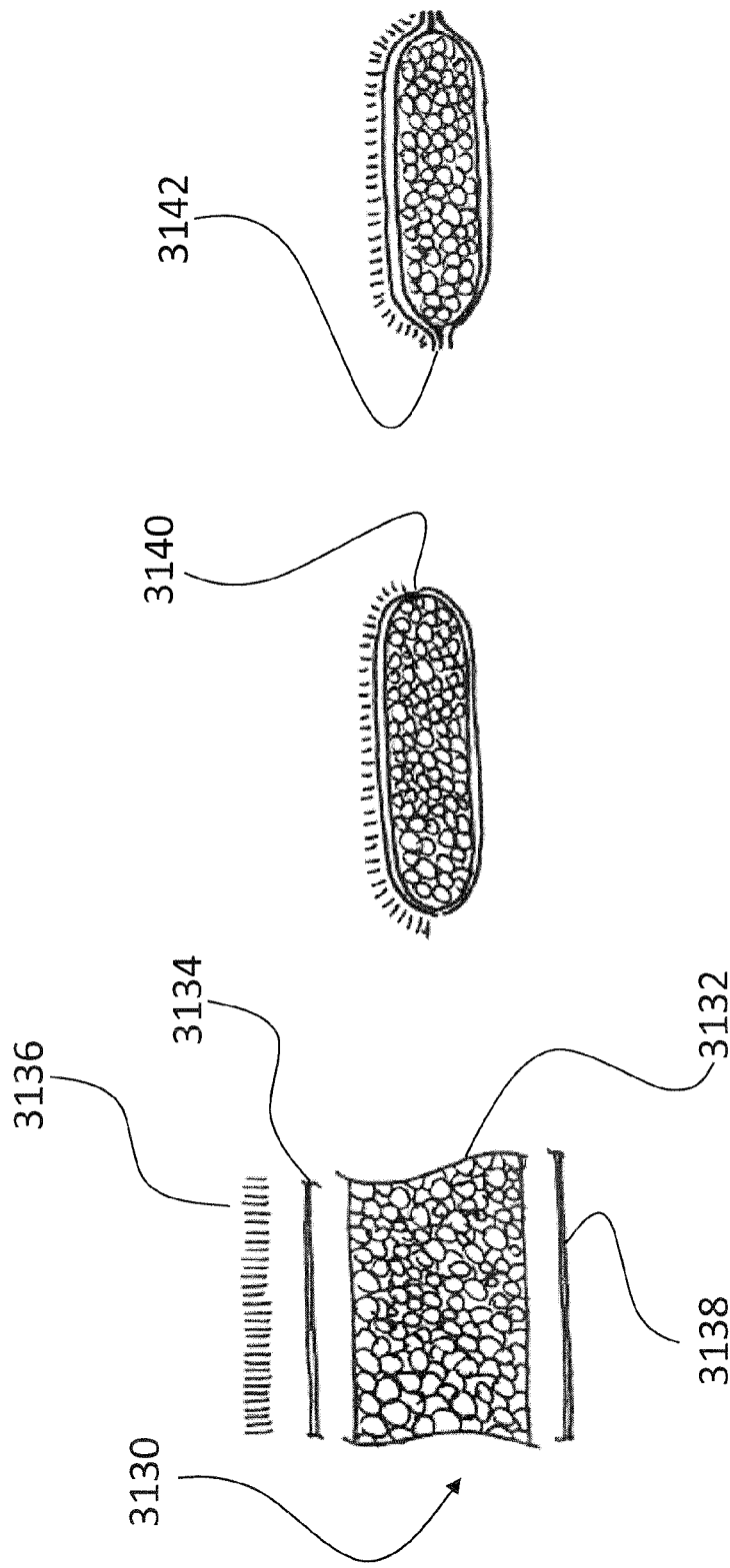

PATIENT INTERFACE COMPONENT

This application is a continuation of U.S. application Ser. No. 15/274,438, filed Sep. 23, 2016, now U.S. Pat. No. 10,967,144, which claims priority to EP 15186945.0, filed 25 Sep. 2015, the entire contents of each of which is hereby incorporated by reference in its entirety.

1 BACKGROUND OF THE TECHNOLOGY

1.1 Field of the Technology

The present technology relates to one or more of the detection, diagnosis, treatment, prevention and amelioration of respiratory-related disorders. The present technology also relates to medical devices or apparatus, and their use. In particular, the present technology relates to parts of a patient interface and an interface including such parts or components being for sealed delivery of a flow of air at a continuously positive pressure with respect to ambient air pressure to an entrance to the patient's airways including at least entrance of a patient's nares. The component and the patient interface are particularly configured to maintain a therapy pressure in a range of about 4 cmH2O to about 30 cmH2O above ambient air pressure in use, throughout the patient's respiratory cycle, while the patient is sleeping, to ameliorate sleep disordered breathing. Particular fields of the present technology, as further discussed below, relate to non-invasive positive pressure ventilation (NIPPY) therapy such as Continuous Positive Airway Pressure (CPAP) therapy.

1.1.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

1.1.2 Therapy

Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient in taking a full breath and/or maintain adequate oxygen levels in the body by doing some or all of the work of breathing. The ventilatory support is provided via a patient interface. NIV has been used to treat CSR, OHS, COPD, MD and Chest Wall disorders. In some forms, the comfort and effectiveness of these therapies may be improved.

1.1.2.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

1.1.2.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the patient's face when force is applied to the patient interface with the seal-forming portion in confronting engagement with the patient's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris, however some patients find these uncomfortable.

Another form of seal-forming portion may use adhesive to achieve a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

1.1.2.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

EP 2691058 EP relates to a Mask cushion for a breathing mask adapted to be used in treatment of sleep disordered breathing, the mask cushion being for contacting the skin of a patient during use, wherein said mask cushion is made of silicone and is adapted to exude a silicone oil contained in the silicone mask cushion release the substances to the patient's skin during use.

2 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

An aspect of certain forms of the present technology is to provide methods and/or apparatus that improve the compliance of patients with respiratory therapy.

One form of the present technology comprises a pad for forming a seal forming structure against a user's skin for use with a patient interface, the pad comprising a substance and being configured to release said substance to the user during use.

The pad preferably comprises a base layer, a fibre layer comprising a plurality of fibres for contacting a patient's skin, and a connection layer for connecting the fibers to the base material.

The base layer and/or the fibre layer is/are preferably adapted to act as a reservoir for substances.

The pad according to the present technology is preferably adapted and arranged for sealed delivery of a flow of air at a continuously positive pressure with respect to ambient air pressure to an entrance to the patient's airways including at least entrance of a patient's nares, wherein the pad and the patient interface are configured to maintain a therapy pressure in a range of about 4 cmH2O to about 30 cmH2O above ambient air pressure in use, throughout the patient's respiratory cycle, while the patient is sleeping, to ameliorate sleep disordered breathing. The pad is preferably suitable for use in patient interfaces for treating a respiratory disorder.

A further aspect of the present technology relates to a set of pads, preferably according to any one of the preceding claims, the set pads comprising two or more pads, the pads preferably comprising different substances.

A further aspect of the present technology relates to Kit comprising one or more pads according to ay one of the present technology, the pad(s) being free of substances, the kit further comprising means for applying a substance to the pad via its surface, in such case the means preferably being a pipette or brush, or into the base layer, in such case the means preferably being a syringe, wherein the kit preferably further comprises one or more substances or information on suitable substances which may be individually selected by the user.

A further aspect of the present technology relates to patient interface comprising a pad, set of pads or kit according to the present technology constituting a sealing structure, the patient interface further comprising a positioning and stabilising structure to maintain the pad in sealing contact with an area surrounding an entrance to the patient's airways while maintaining a therapeutic pressure at the entrance to the patient's airways; a plenum chamber pressurised at a pressure above ambient pressure in use; a gas washout vent configured to allow a flow of patient exhaled CO2 to an exterior of the patient interface to minimise rebreathing of exhaled CO2 by the patient.

A further aspect of the present technology relates to an apparatus for treating a respiratory disorder comprising a patient interface as referred to above, an air circuit; and a source of air at positive pressure.

Another aspects of one or more forms of the present technology relate to an interface mechanisms of a/the pad towards a patient, plenum chamber and mask structure, to a physical composition of the reservoir, to structural properties of the release mechanism, to physical properties of the substances, and a set or kit of the aspects discussed herein.

Further preferred aspects of the present technology will become apparent from the following list of aspects:

1. A pad for forming a seal forming structure against a user's skin for use with a patient interface, the pad comprising
   a base layer
   a fibre layer comprising a plurality of fibers for contacting a patient's skin,
   and a connection layer for connecting the fibers to the base material,
   wherein the base layer and/or the fibre layer is/are adapted to act as a reservoir for substances.
2. The pad according to aspect 1, the pad being for sealed delivery of a flow of air at a continuously positive pressure with respect to ambient air pressure to an entrance to the patient's airways including at least entrance of a patient's nares, wherein the pad and the patient interface are configured to maintain a therapy pressure in a range of about 4 cmH2O to about 30 cmH2O above ambient air pressure in use, throughout the patient's respiratory cycle, while the patient is sleeping, to ameliorate sleep disordered breathing.

3. The pad according to aspect 1 or 2, the pad being suitable for use in patient interfaces for treating a respiratory disorder.

4. The pad according to any one of the preceding claims, wherein the connection layer is a membrane layer allowing a substance to migrate into and/or out of the base layer.

4.a The pad according to any one of the preceding aspects, wherein the connection layer is barrier layer to a substance but allowing the substance to migrate, preferably at a predefined rate into and/or out of the base layer.

4.b The pad according to any one of the preceding aspects, wherein the substance may be provided from the base layer to the patient by application of one or more physical effects, such as migration, concentration differences, capillary forces, pressure differences, and/or membrane effects.

5. The pad according to any one of the preceding aspects, wherein the connection layer is a separate layer or an integral layer of the base layer.

6. The pad according to any one of the preceding aspects, wherein the base material comprises a base surface and wherein the plurality of fibers is fixed to and extends away from said base surface for contacting a patient's skin.

7. The pad according to any one of the preceding aspects, wherein the base layer is made of a foam material.

7.a The pad according to any one of the preceding aspects, wherein the base layer is made of a resilient foam, preferably an open cell foam and/or more preferably not a closed-cell foam and/or not a silicone foam.

8. The pad according to any one of the preceding aspects, wherein the pad is adapted to be connected to a cushion.

9. The pad according to any one of the preceding aspects, wherein the plurality of fibers is made from any one from the group consisting of: cotton, wool, viscose, nylon, and cellulose.

10. The pad according to any one of the preceding aspects, wherein the plurality of fibers is in fluid communication with the base layer.

11. The pad according to any one of the preceding aspects, wherein the fibers and/or the base layer is adapted to release the substance to the skin of a patient.

12. The pad according to any one of the preceding aspects, wherein the intermediate layer has an adjusted permeability to allow controlled speed of substance migration therethrough.

12.b The pad according to any one of the preceding aspects, wherein the intermediate layer allows a predefined/limited flow rate of the substance therethrough.

13 The pad according to any one of the preceding aspects, wherein the flow or migration of substance through the intermediate layer may lead to a pressure increase inside the base layer in response to a volume reduction as the base layer gets compressed.

14. The pad according to any one of the preceding aspects, wherein the connection layer comprises a micro-porosity, small openings or macro-porosity, or is adapted to allow diffusion at a chemical level.

14.a The pad according to aspects 14, wherein the openings or porosity is achieved by mechanical treatment, e.g., by needles, or created by thermal effects, e.g., laser.

15. The pad according to any one of the preceding aspects, wherein the fibre layer and/or the fibres are adapted to serve as a "wick" to enable substance to migrate from the base layer to the patient's skin.

16. The pad according to any one of the preceding aspects, wherein the 'volume' of the fibre layer, i.e., the spaces between the fibers serves as a reservoir or sponge which holds the substance and/or wherein the base layer serves as a reservoir for holding the substance wherein the fibre layer serves as a buffer for the already released substance before it contacts the user's skin.

17. The pad according to any one of the preceding aspects, further comprising a substance contained in the fiber layer and/or the base layer.

18. The pad according to any one of the preceding aspects, wherein the connection layer and substance are selected such that the connection layer is not dissolved by said substance.

19. The pad according to any one of the preceding aspects, wherein the substance does not contain any solvents and, preferably, does not dissolve PUR foam.

20. The pad according to any one of the preceding aspects, wherein the base material is adapted to conform to a patient's face.

21. The pad according to any one of the preceding aspects, wherein the intermediate layer also serves as a connection layer for connecting the fibres of the fibre layer to the base layer or wherein there is provided an additional adhesive layer for connecting the fibres of the fibre layer to the base layer and/or the intermediate layer.

22. The pad according to any one of the preceding aspects, wherein the base material, on a surface opposing the connection layer, comprises an adhesive layer, preferably for removably adhering the pad to an underlying cushion.

23. The pad according to the preceding aspect, further comprising a release liner covering said adhesive layer.

24. The pad according to any one of the preceding aspects, wherein the fibres are flocked onto the base layer, the intermediate layer and/or an adhesive layer.

25. The pad according to any one of the preceding aspects, wherein the fibers have a length of between about 0.01 and 5.0 mm, more preferably between about 0.05 and 2.0 mm and most preferably between about 0.1 and 1.0 mm 26. The pad according to any one of the preceding aspects, wherein the pad has a thickness of between about 0.5 to 26 mm, preferably between about 1.0 to 13 mm, more preferably between about 2 and 10 mm, and most preferably between 4 and 8 mm 27. The pad according to the preceding aspect, wherein the base layer has a thickness of about more than 50%, preferably more than 75% and more preferably of about more than 90% of the pad thickness.

28. The pad according to any one of the preceding aspects, wherein the base material has a generally ring-like geometry.

29. The pad according to any one of the preceding aspects, the pad being contained in a package, the package being air tight.

30. The pad according to any one of the preceding aspects, the substance being a scented substance and being contained in the fibre layer, not to the base layer.
31. The pad according to any one of the preceding aspects, the substance being a powder substance applied to the fibre layer, not to the base layer, the powder substance preferably, acting as an ointment and, more preferably, being activated by the skin moisture.
32. The pad according to any one of the preceding aspects, the substance being a gel or oil being contained in the base layer and preferably being released as the foam is compressed during use,
33. The pad according to any one of the preceding aspects, wherein the substance has a "sticky" character to improve mask sealing performance.
34. The pad according to any one of the preceding aspects, wherein the substance is adapted to act as an adhesive when being released in use of the pad for reacting with skin moisture or ambient air to establish a (releasable) adhesive bond with the patient's face.
35. The pad according to any one of the preceding aspects, wherein the substance is of high viscosity, such as a high-viscosity gel, and is applied to the fibre layer, for sticking to the patient's face in use.
36. The pad according to any one of the preceding aspects, wherein the substance is of low viscosity, contained in the reservoir, and released from there in use, the substance solidifying upon release to become of higher viscosity, preferably upon contact with skin moisture or ambient air.
37. The pad according to any one of the preceding aspects, wherein the substance has a "slippery" character to reduce friction between skin and cushion to reduce pressure sores, such substance preferably being an oil-based substance of low to medium viscosity.
38. The pad according to any one the preceding aspects, pad being for use with a patient interface comprising a nasal cushion, a nasal pad, a mouth cushion, a facial or nose and mouth cushion, a forehead cushion or forehead pad.
39. The pad according to the preceding aspect, the pad being larger than and/or extending beyond the contact region of the underlying patient interface cushion structure.
40. The pad according to any one of the preceding aspects, wherein the substance is/has a selected scent, a skin care substance, for example regenerating, soothing, anti-inflammatory, a beauty product, for example anti-aging, revitalizing, a lotion to reduce redness or pressure sores, a lotion with a cosmetic effect, a powder, an oil, a low-viscosity gel, is not a high-viscosity substance, is not a cream, does not contain solvents, has a therapeutic effect related to issues arising with frequent mask usage, such as skin irritation, skin damage, makes mask more pleasant to wear, for example by providing improved odor or tactile feel for the patient, and/or has beneficial effects on mask seal, comfort and/or stability.
41. The pad according to any one of the preceding aspects, wherein the substance is a powder, having a grain size no larger than 0.1 mm or wherein the substance is an oil or gel having a viscosity of less than 20 mm$^2$/s, preferably at 20° C. temperature.
42. The pad according to any one of the preceding aspects, wherein the base layer material has a weight in the range from 5 kg/m$^3$ to 100 kg/m$^3$, preferably from 15 kg/m$^3$ to 60 kg/m$^3$, further preferably from 25 kg/m$^3$ to 40 kg/m$^3$ and moreover preferably of about 30 kg/m$^3$.
43. The pad according to any one of the preceding aspects, wherein the preferred porosity of the base layer material ranges from about 25.4 to about 127 foam cells per inch (2.54 cm), more preferably from about 50 to about 100 foam cells per inch (2.54 cm), and also preferably from about 70 to 80 foam cells per inch (2.54 cm) and also preferably about 75 foam cells per inch (2.54 cm).
44. The pad according to any one of the preceding aspects, wherein the average pore diameter ranges from about 1 to 0.2 mm, also preferably from about 0.51-0.25 mm, and also preferably from about 0.36 0.32 mm and also preferably about 0.34 mm
45. The pad according to any one of the preceding aspects, wherein the intermediate layer has a pore size ranging from about 0.05 mm to about 1.0 mm, preferably from about 0.1 mm to about 0.5 mm, more preferred from about 0.15 mm to about 0.3 mm and more preferred of about 0.2 mm
46. The pad according to any one of the preceding aspects, wherein the intermediate layer has a pore size of about 0.1 μm to about 50 μm, preferably from about 0.3 μm to about 25 μm, more preferred from about 0.5 μm to about 5 μm and also preferred of about 1.0 μm.
47. The pad according to any one of the preceding aspects, wherein the substance has a viscosity (at 20° C. ambient temperature) of such from about 1.0 mPa*s to about 10$^4$ mPa*s, preferably from about 5 mPa*s to about 100 mPa*s, and further preferred from about 10 to about 100 mPa*s, preferably at 20° C. temperature.
48. The pad according to any one of the preceding aspects, wherein the substance has a viscosity (at 20° C. ambient temperature) of from about 0.5 mPa*s to about 11$^3$ mPa*s, preferably from about 2.5 mPa*s to about 80 mPa*s, and further preferred from about 5 to about 50 mPa*s.
49. The pad according to any one of the preceding aspects, wherein the release rate per mm$^2$ of contact surface is between about 0.01 mg/hr and about 10 mg/hr, preferably between about 0.5 mg/hr and about 5 mg/hr, and also preferred of about 0.1 mg/hr.
50. A set of pads, preferably according to any one of the preceding aspects, the set pads comprising two or more pads, the pads preferably comprising different substances.
51. A Kit comprising one or more pads according to any one of the preceding aspects, the pad(s) being free of substances, the kit further comprising means for applying a substance to the pad via its surface, in such case the means preferably being a (pipette or brush, or into the base layer, in such case the means preferably being a syringe, wherein the kit preferably further comprises one or more substances or information on suitable substances which may be individually selected by the user.
52. A patient interface comprising a pad, set of pads or kit according to any one of the preceding aspects constituting a sealing structure, the patient interface further comprising,
a positioning and stabilising structure to maintain the pad in sealing contact with an area surrounding an entrance to the patient's airways while maintaining a therapeutic pressure at the entrance to the patient's airways;
a plenum chamber pressurised at a pressure above ambient pressure in use;
a gas washout vent configured to allow a flow of patient exhaled CO2 to an exterior of the patient interface to minimise rebreathing of exhaled CO2 by the patient.

53. Apparatus for treating a respiratory disorder comprising:
a patient interface as claimed in aspect 50;
an air circuit; and
a source of air at positive pressure.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Treatment Systems

FIG. 1a shows a system including a patient 1000 wearing a patient interface 3000, in the form of a nasal pillows, receiving a supply of air at positive pressure from an RPT device 4000. Air from the RPT device is humidified in a humidifier 5000, and passes along an air circuit 4170 to the patient 1000. A bed partner 1100 is also shown.

3.2 Respiratory System and Facial Anatomy

Figure 1A:
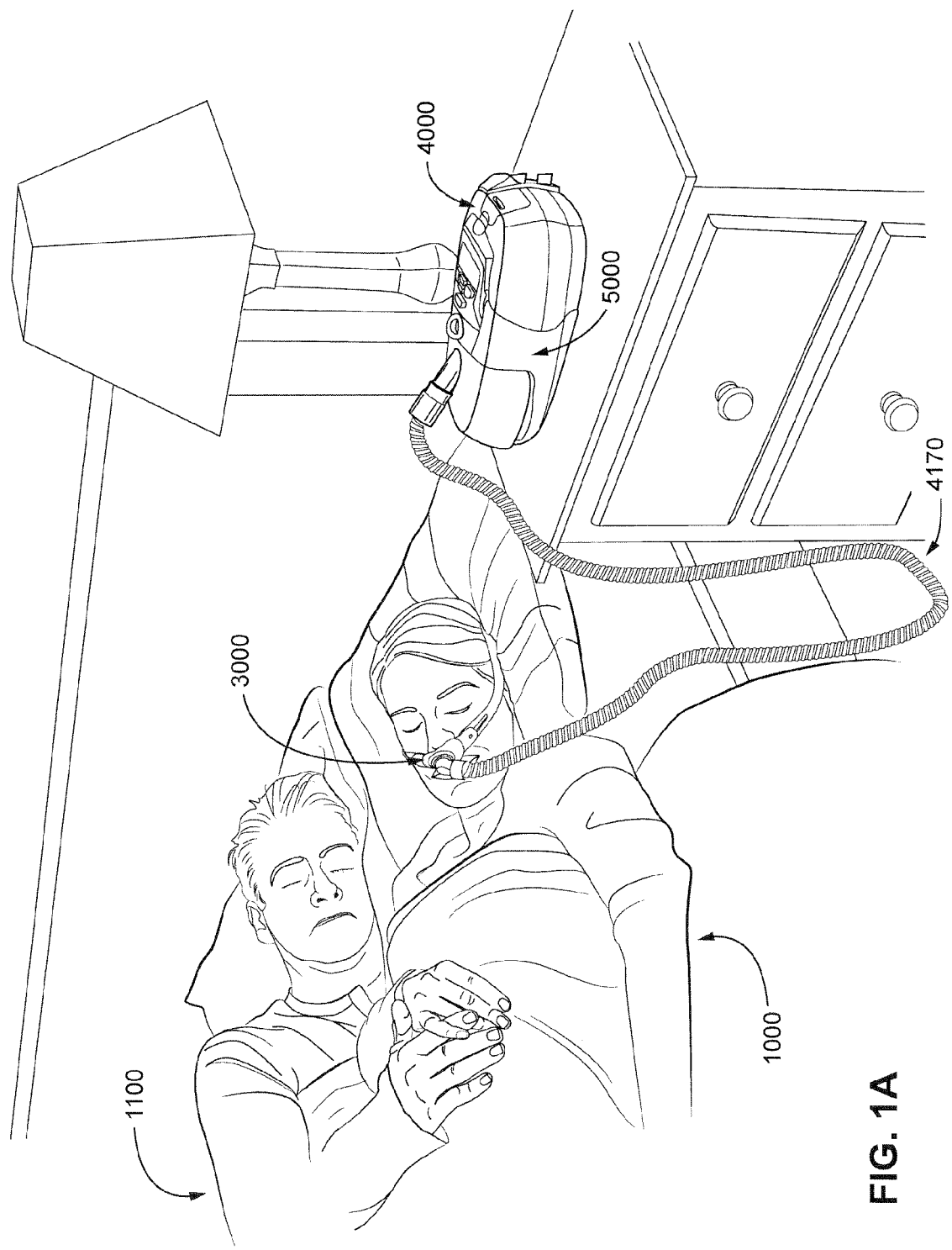
FIG. 1b shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
FIG. 1c shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 1B:
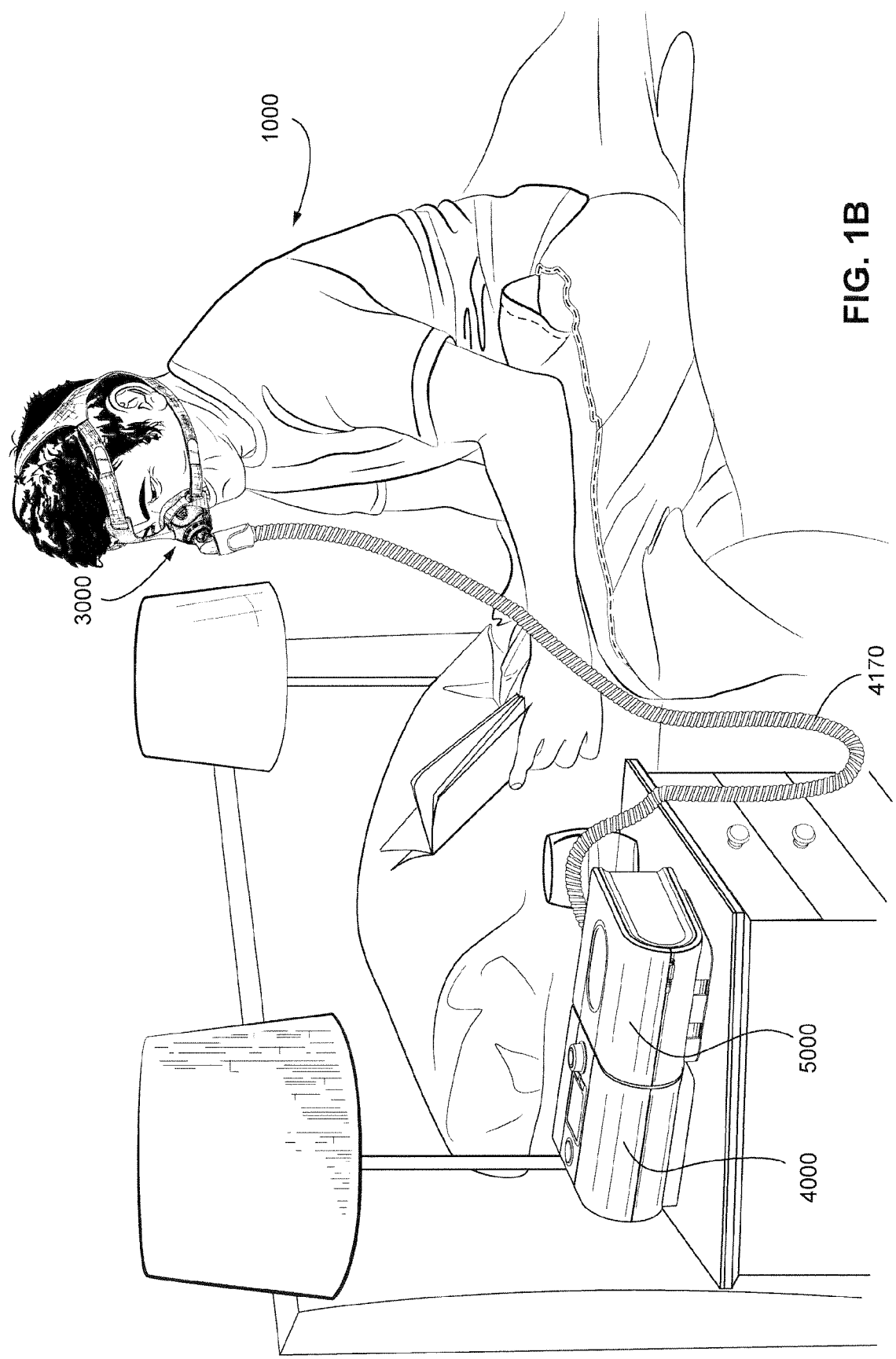
Figure 1C:
Figure 2A:
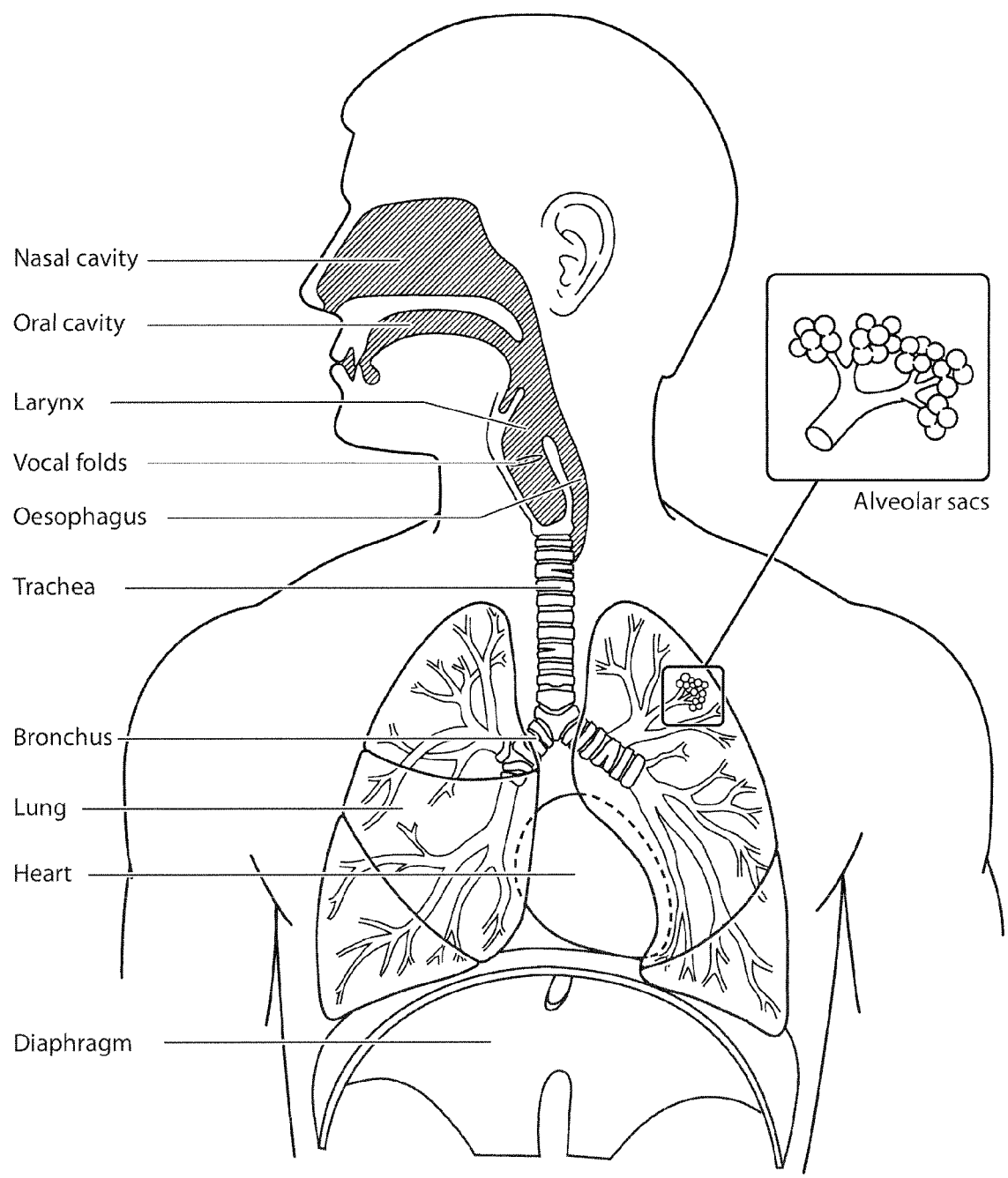

FIG. 2a shows an overview of a human respiratory system including the nasal and oral cavities, the larynx, vocal folds, oesophagus, trachea, bronchus, lung, alveolar sacs, heart and diaphragm.

Figure 2B:
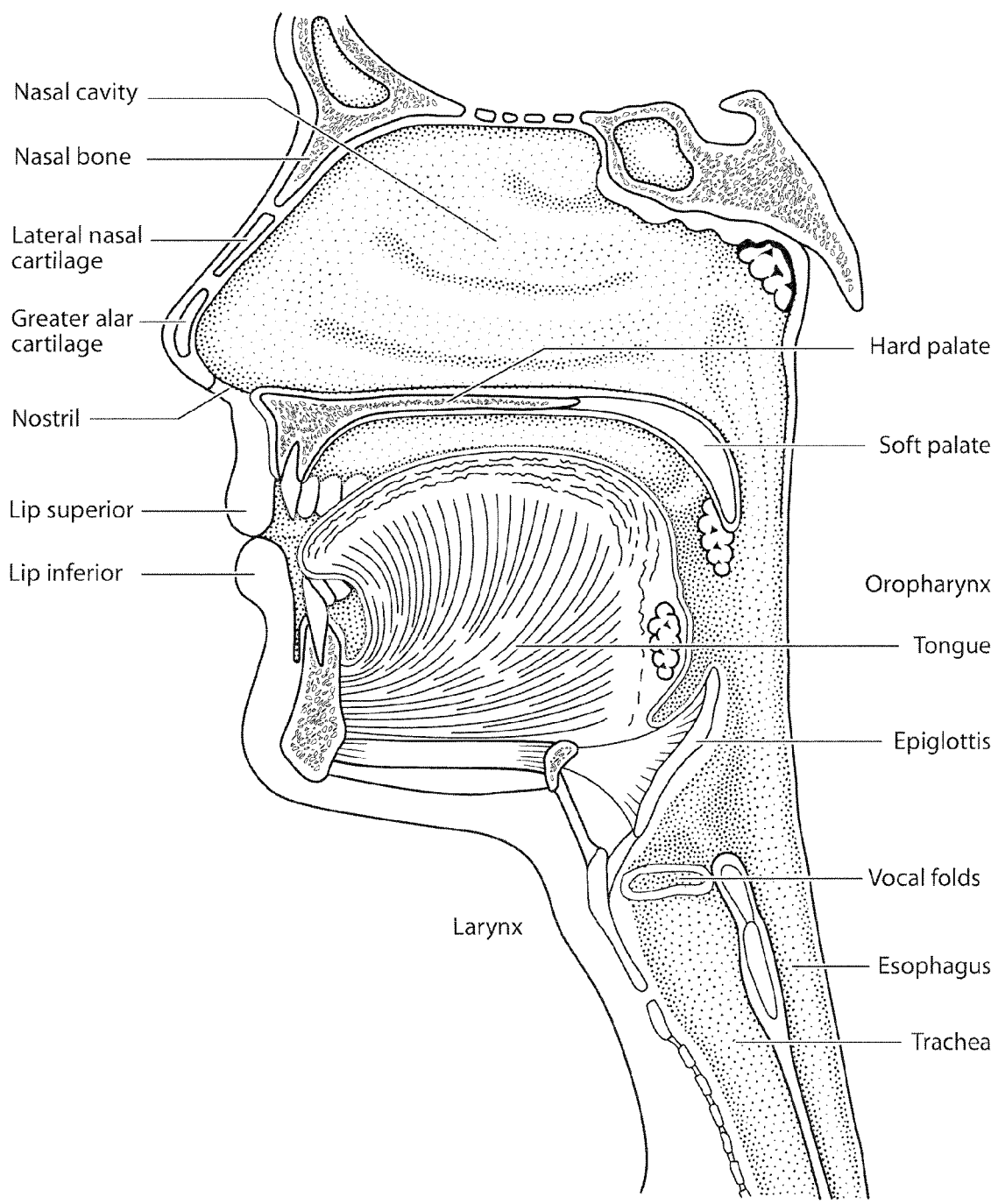

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
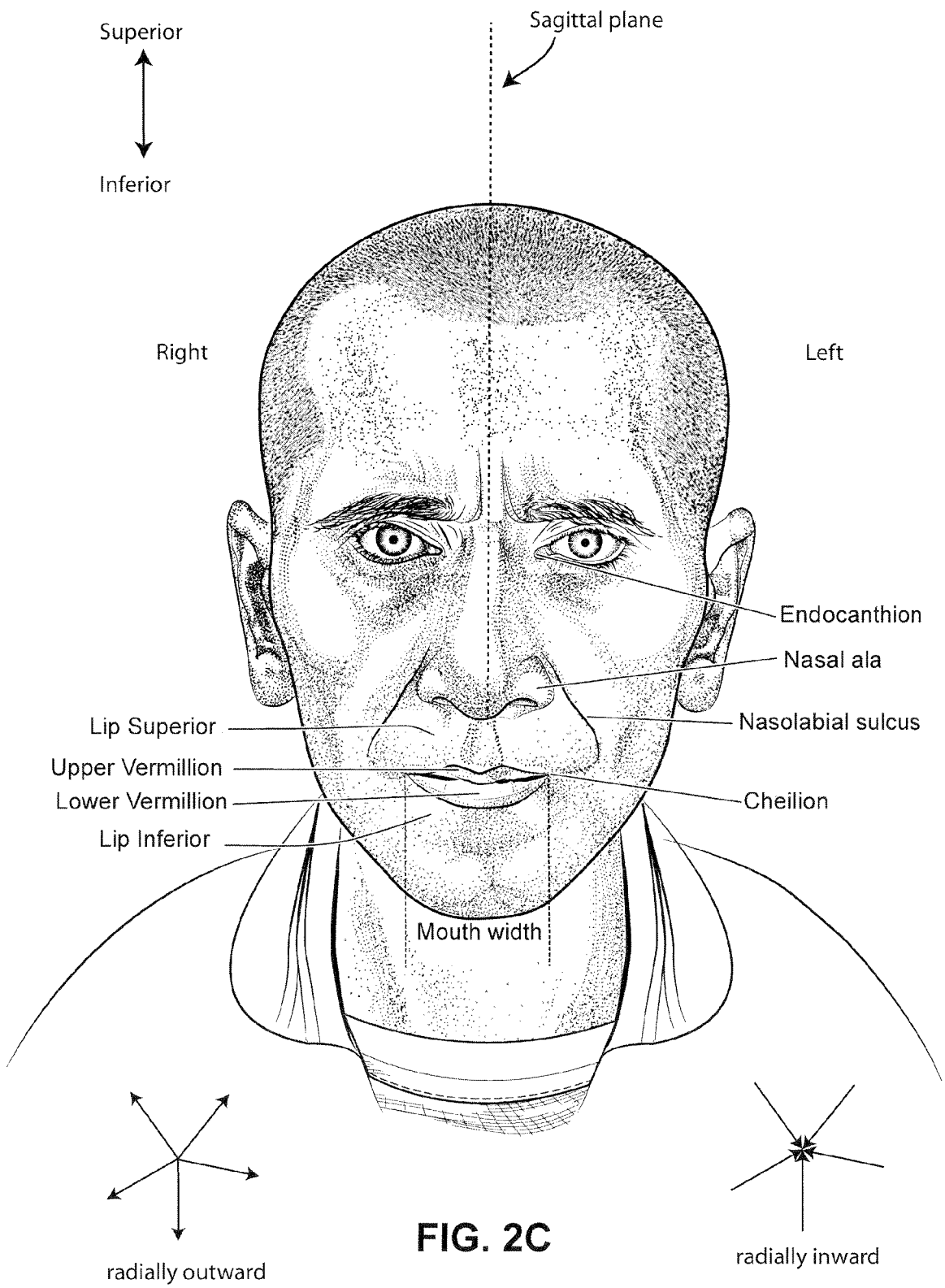

FIG. 2c is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
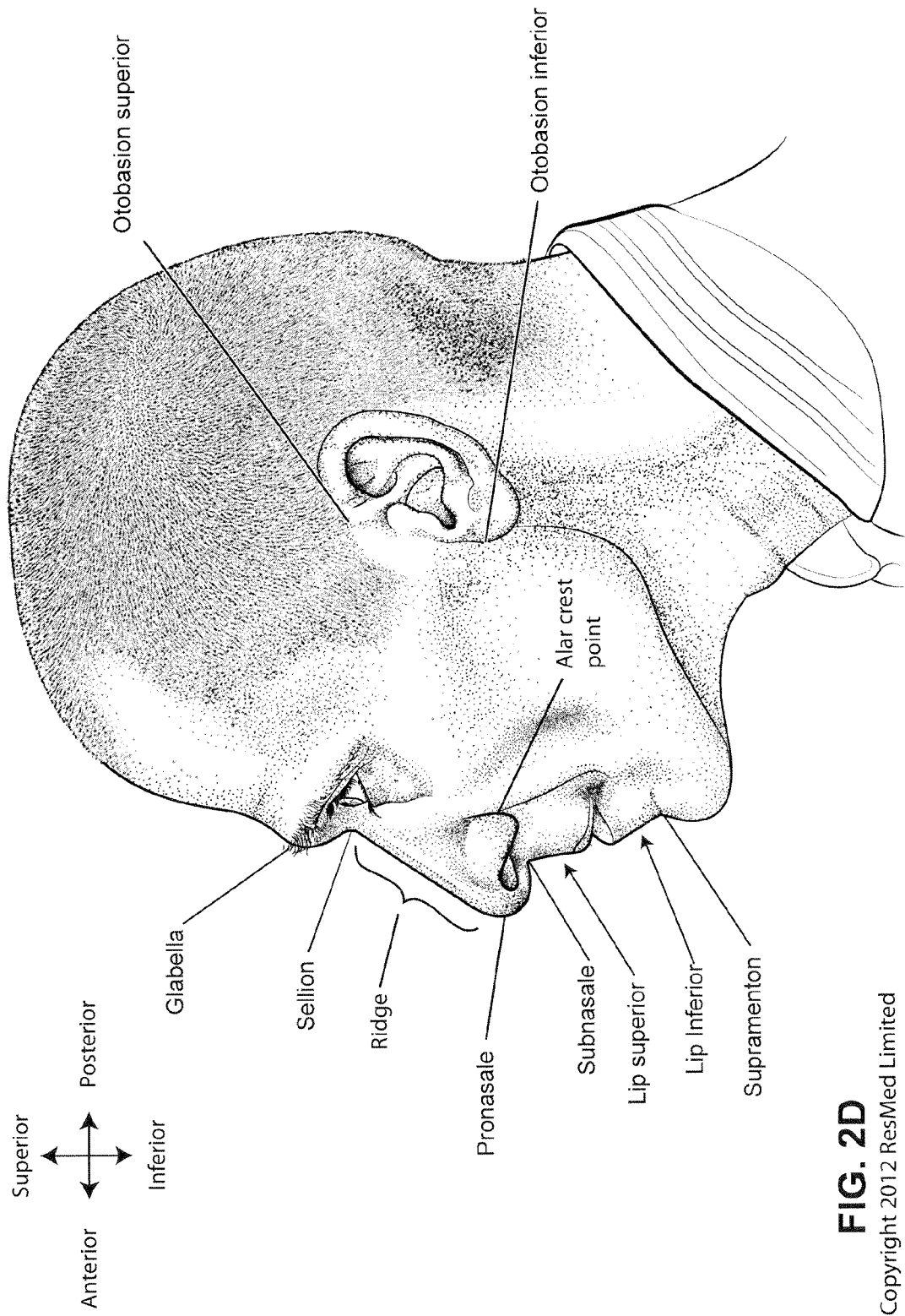

FIG. 2d is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

3.3 Patient Interface

Figure 3A:
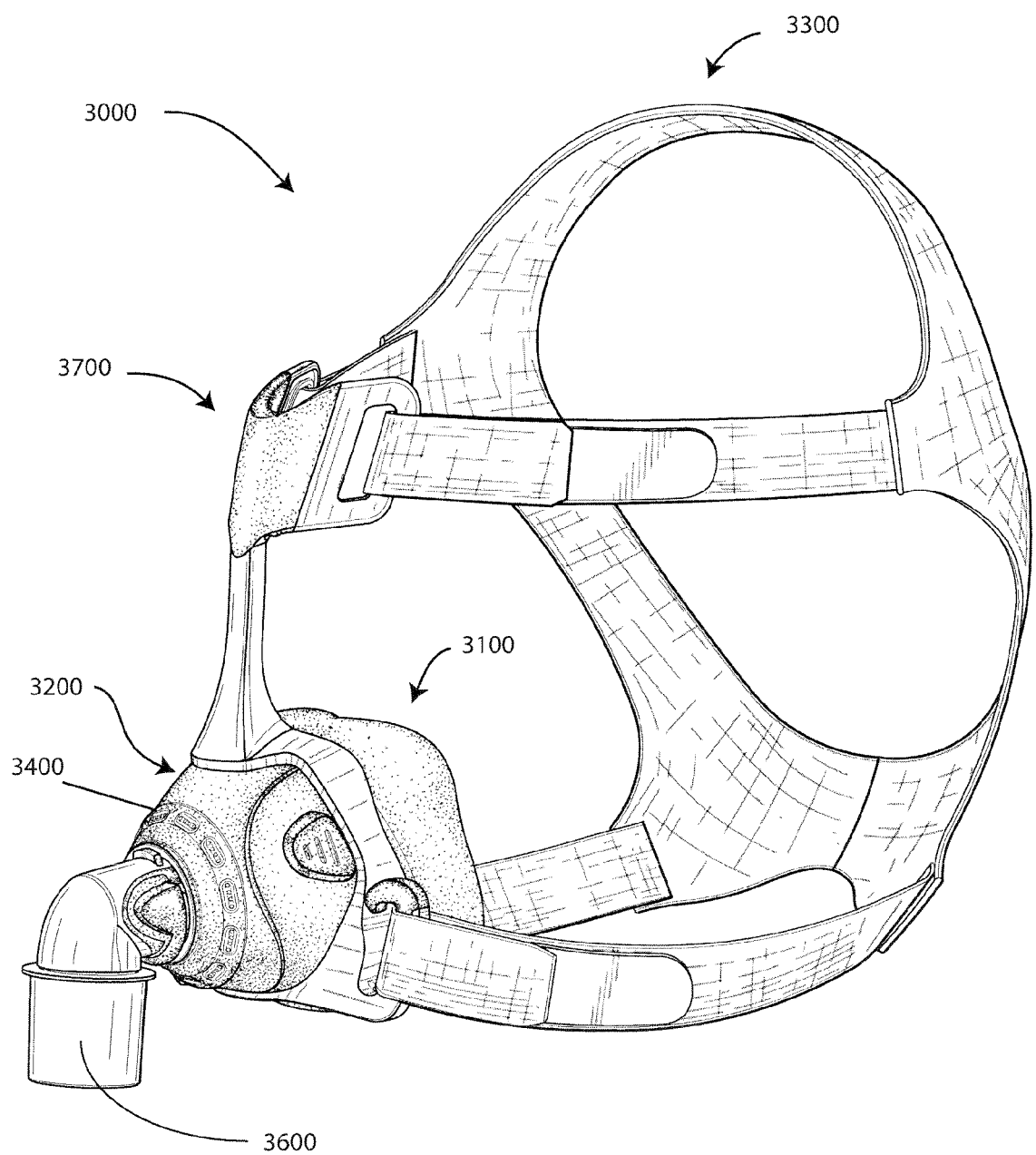

FIG. 3a shows a patient interface in the form of a nasal mask in accordance with one form of the present technology.

FIGS. 4a to 4c show exemplary cross sections of pads according to the present technology.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

4.2 Patient Interface

A non-invasive patient interface 3000 in accordance with one aspect of the present technology comprises the following functional aspects: a seal-forming structure 3100, a plenum chamber 3200, a positioning and stabilising structure 3300 and one form of connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

4.2.1 Seal-Forming Structure

In one form of the present technology, a seal-forming structure 3100 provides a seal-forming surface, preferably for sealing against a patient's skin, and may additionally provide a cushioning function.

A seal-forming structure 3100 in accordance with the present technology may be constructed from a soft, flexible, resilient material such as polyurethane.

In one form, the seal-forming structure 3100 comprises a sealing flange 3110 and a support flange 3120. The sealing flange 3110 comprises a relatively thin member with a thickness of less than about 1 mm, for example about 0.25 mm to about 0.45 mm, that extends around the perimeter 3210 of the plenum chamber 3200. Support flange 3120 may be relatively thicker than the sealing flange 3110. The support flange 3120 is disposed between the sealing flange 3110 and the marginal edge 3220 of the plenum chamber 3200, and extends at least part of the way around the perimeter 3210. The support flange 3120 is or includes a spring-like element and functions to support the sealing flange 3110 from buckling in use. In use the sealing flange 3110 can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

The seal-forming structure 3100 of the present technology preferably has a pad like structure. Preferably, the seal-forming structure 3100 provides a seal-forming surface while cooperating with a cushioning structure or undercushion to provide a cushioning function, as further discussed below and, e.g., as discussed in EP 14 17 2818.8 and U.S. Ser. No. 14/741,930, which are incorporated herein by reference. The seal-forming structure may provide a macro-cushioning function and/or a micro-cushioning function, particularly depending on its dimension and physical properties, e.g. as regards resiliency. In preferred aspects of the present technology, the seal-forming structure is comparatively thin and may not adapt to different facial topographies of the patients in a satisfactory way still allowing proper sealing. However, it may advantageously still provide a micro adjustability allowing to optimize, in conjunction with an underlying macro-cushioning and adaptation structure, to provide an optimized sealing for different facial geometries.

The seal-forming structure 3100 according to the present technology may advantageously be used in all forms as addressed above, e.g., independent of geometry of the cushioning structure or sealing surface. It may be used with nasal pillows or puffs as well as with sealing structures sealing on an upper lip region (that is, the lip superior) or on a chin-region of the patient's face. The seal-forming structure may, e.g., either replace sealing flange 3110 or be connected thereto.

According to a further preferred aspect of the present technology, the pad does not need to be used as a seal-forming structure but also in applications not requiring sealing contact. Such applications may include but are not limited to the face contacting portion or cushion of forehead support structures. The pad may be adapted to conform to a user's face.

A pad structure according a preferred aspect of the present technology is shown in FIGS. 4a to 4c. The pad 3130 comprises a base layer 3132, a connection layer 3234 and a fibre layer 3136. The connection layer 3134 preferably being sandwiched between the base layer 3132 and the fibre layer 3136. FIGS. 4a to 4c also show the provision of an, preferably adhesive, backing layer 3138. While FIG. 4a shows an exploded view of said layers in cross section, FIG. 4b shows a cross section of a preferred pad having a first preferred edge joint variant 3140, which may be achieve by methods of the kind known as 'kiss-cut', in which the end faces of layers 3138 and 3234 and/or 3136 touch or closely touch. FIG. 4c shows a cross section of a preferred pad having a second preferred edge joint variant 3142, which may be achieved by, e.g., welding, cold welding or pressing before die cutting, in which the ends of layers 3138 and 3234 and/or 3136 overlay and are connected to one another.

The base layer 3132 is preferably suitable and/or adapted for acting as a reservoir for a substance (not shown), as will be further discussed below.

The base layer 3132 preferably is made of, i.e. comprises or consists, a foam material, preferably a resilient foam, preferably an open-cell foam. Further preferred, the base layer does not consist of or does not-comprise a closed-cell foam.

The base layer 3132 is preferably made of Polyurethane (PU or PUR) foam. Also preferably, the base layer is not made of silicone or silicone foam.

The foam base layer 3132 has a porosity as typically encountered within open-cell foams, such as PU/PUR foam. Such porosity, may be described as the specific weight of the foam (based on the material's density), or as a ratio of material to air content.

For the present technology, a large content of air in the foam is desirable and was found to improve the base layer's capability for acting as a reservoir for substances. It is understood that more and bigger air cells (pores) can contain larger amounts of substance. Besides the overall amount of or ratio of air in the foam, also the average pore size is believed to contribute to the base layer's properties as regards receiving and releasing of substances.

A preferred density of the base layer material has been found to range from 5 kg/m$^3$ to 100 kg/m$^3$, preferably from 15 kg/m$^3$ to 60 kg/m$^3$, further preferably from 25 kg/m$^3$ to 40 kg/m$^3$ and moreover preferably about 30 kg/m$^3$.

A preferred porosity of the base layer material has been found to range from about 25.4 to about 127 foam cells per inch (2.54 cm), more preferably from about 50 to about 100 foam cells per inch (2.54 cm), and also preferably from about 70 to 80 foam cells per inch (2.54 cm) and also preferably about 75 foam cells per inch (2.54 cm). Such porosity may be calculated to result in a preferred average pore diameter of about 1 to 0.2 mm, also preferably from about 0.51-0.25 mm, and also preferably from about 0.36 0.32 mm and also preferably about 0.34 mm Preferably, the above ranges refer to average pore sizes.

The base layer preferably has a thickness being the majority of the pad's thickness. Preferably, the base layer's thickness is more than 50%, more preferred more than 75%, furthermore preferred more than 85% and even further preferred more than 95% of the pad's thickness.

In this context, it is noted that the pad according to the present technology preferably has a pad thickness of between about 1.5 mm to 26 mm, preferably between about 3.0 mm and 13 mm.

The intermediate layer 3134, located between the fibres and the base layer. The intermediate layer preferably connecting the fibres of the fibre layer 3136 to the base layer 3132. The intermediate layer may also be referred to a connection and/or migration layer.

As indicated above, the intermediate layer 3134 preferably serves as a connection layer for connecting the fibre layer 3136 to the base layer 3132. Alternatively or additionally, the connection layer serves as a membrane layer or barrier layer to the substance while allowing a substance to flow or migrate there through, preferably at a predefined rate. The intermediate layer may allow the substance to flow, at a limited and preferably predefined flow rate, from the base layer acting a reservoir to the fibre layer. The intermediate layer 3134 therefore exhibits a limited flow rate and/or an adjusted permeability. According to a preferred aspect of the present technology, thus limited flow rate and/or adjusted permeability is to be considered in combination with the specific substance involved, as will also be apparent from the further discussion. In again other words, the physical properties of the intermediate layer are such that the fibre layer is in fluid communication with the base layer.

As indicated, the properties of the intermediate layer, as such and/or in combination with the properties of the base layer, the substance, and/or the fibre layer, that a predefined/limited flow rate of the substance therethrough is achieved. One aspect assisting flow of the substance through the intermediate layer may be a pressure increase inside the base layer occurring in response to a volume reduction as the base (preferably foam) layer gets compressed when the pad is, in use, pressed against the user's face. This predefined or limited flow rate may advantageously prevent the substance from being released immediately when the pad is put under pressure since the substance is forced to dissipate out of the reservoir at a slow(er) rate.

The referenced flow limitation may, e.g., be achieved by i) micro-porosity; ii) small openings (mechanically created e.g. by needles or created by thermal effects e.g. laser; iii) or due to diffusion at a chemical level.

For example, such limited flow rate and/or adjusted permeability may be achieved by providing the intermediate layer, preferably as such being impermeable to the substance, with a predefined porosity. The intermediate layer may thus be configured as a layer having a range of small openings to allow a substance to travel from within the base layer or reservoir to the patient contacting surface, i.e. preferably the fibre layer.

The size of these openings are preferably smaller than the pores or the pore diameter in the base layer so that the intermediate layer's permeability to the substance is, preferably substantially, lower than that of the base layer or reservoir itself, i.e. preferably, the permeability or flow of the substance through the surface of the base layer contacting the intermediate layer. As also discussed below, the base layer preferably has a sealed outer surface or outer layer apart from at the contact area of the intermediate layer, preferably to avoid the substance flowing to other places than to the fibre layer and the user's face. For example, an adhesive layer 3138 for connecting the pad to the mask cushion may be provided which forms an essentially impermeable layer; the intermediate layer and the adhesive backing 3138 are joined by a manufacturing process, such as cold welding, to create a rounded (side) edge, whereby the substance within the reservoir cannot migrate sideways or towards the mask.

These openings may be manufactured, e.g., by mechanical means such as needles, by laser machining, or may be formed by the intermediate layer's chemical properties themselves. Also, a mesh-reinforced intermediate layer or a foamed layer may be used. As indicated above, the intermediate layer may, in addition to or alternative to providing an adjusted permeability or limited flow rate, exhibit adhesive properties or be an adhesive for attaching the fibre layer or the fibres of the fibre layer to the base layer. According to a preferred aspect of the present technology, an adhesive layer for attaching the fibre layer or the fibres of the fibre layer may be provided in addition to the intermediate layer and preferably between the intermediate layer and the fibre layer. In addition or alternatively, the intermediate layer may be formed integrally with the base layer in a structural or functional way. Such structural integrity may be achieved, e.g., by providing a skin or skin layer to the intermediate layer exhibiting the above described preferred properties. A functional integrity may be achieved, e.g., by adapting the base layer such that it inherently, i.e., by itself, exhibits the above described preferred properties, particularly the adjusted permeability and/or limited flow rate, e.g., in that is only sets free a limited amount of substance per time.

According to one aspect of the present technology, the intermediate layer may have a pore size ranging from about 0.05 mm to about 1.0 mm, preferably from about 0.1 mm to about 0.5 mm, more preferred from about 0.15 mm to about 0.3 mm and more preferred of about 0.2 mm Due to the random distribution of pore shapes and pore sizes within the foam, the diameter is preferably averaged over the pores present in a certain direction over a certain length, preferably an inch, each time measured in the direction. E.g., a pore may be more elliptical whereas another adjacent pore may be more spherical, yet in the direction of measurement both may have a similar diameter. Preferably, the above values refer to average pore sizes Alternatively, the intermediate layer may be configured as a solid closed layer, i.e. without pores as referred to above, on a macroscopic level (such as a membrane), while its structure on a microscopic scale may be that of a mesh, or of interconnected molecular chains. In other word's the intermediate layer may be provided with pores on a microscopic/molecular level. Such pores may allow a permeability on a molecular level.

Such pores or openings may be such that they permit all of the contents of the substance to travel from the base layer or reservoir to the fibre layer or patient contacting surface by passing through these pores of the intermediate layer.

A preferred pore size according to this aspect is in the range from about 0.1 µm to about 50 µm, preferably from about 0.3 µm to about 25 µm, more preferred from about 0.5 µm to about 5 µm and also preferred of about 1.0 µm.

According to preferred aspects of the present technology, the diffusivity of the intermediate layer may be configured such that the required flow rate is achieved when the pad is worn by a user.

The fibre layer 3136 is preferably suitable and/or adapted for acting as a reservoir for a substance (not shown). The fibre layer 3136 comprises a plurality of fibres for contacting a patient's skin and, preferably, for sealing against the patient's skin.

According to preferred aspects of the present technology, the fibre layer comprises a plurality of fibres, filaments and/or threads, preferably attached to said base layer, preferably a base surface of said base layer, the base surface facing towards the user in a position of use, and, preferably, facing a patient's face during use. The plurality of fibers, filaments and/or threads is herein also referred to as a plurality of fibers. The plurality of fibers may extend away from said base surface. Preferably, the plurality of fibers is fixed to said base layer, preferably by means of the intermediate layer and/or a fixation or an adhesive layer. The fibers may extend away from said base layer for contacting, preferably sealingly, a user's skin.

The seal forming structure may provide an improved tactile experience and may be more pleasant to wear. The user may more likely and more often use the patient interface and/or may be able to wear it for extended time periods without experiencing adverse effects such as redness, pressure sores etc. The seal forming structure having a plurality of fibers extending away from said base surface and contacting a user's skin may allow for improved sweat dissipation through the fibers. The seal forming structure may improve the ventilation of the contact surface. The fibers may create a kind of slight, diffused leakage, preferably across the entire sealing surface. This diffused leakage may be perceived by users as a cooling, pleasant feeling, as opposed to a localized, punctual leakage often present in common patient interfaces using membranes, which is perceived as disturbing. Furthermore, the fiber length of the plurality of fibers may, in combination and in balance with the width of the contact surface and the sealing force applied by the pad's preferred features to be later discussed herein, such as a suitably designed undercushion to which the pad may be applied, be specified such that a slight and diffused pleasant, cooling leakage perception is promoted, without drifting off into a too large leak rate which may otherwise be perceived as a poor seal. Moreover, the seal forming structure may improve the self-positioning of the patient interface, preferably in the nose region. This may be achieved, e.g., by a particular and preferred orientation of the fibers and/or by the lower coefficient of friction between fibers and the patient's skin, particularly compared to traditional silicone membranes. Silicone membranes, for instance, may have a tendency to adhere to the skin, so the user effectively has to lift the cushion off the skin and re-position it. Fibers may have a much lower tendency to adhere to the user's skin; therefore the mask cushion may be repositioned without removing it from the face, even during therapy. In addition, and as further discussed herein, the fibre layer and its fibres advantageously assist in storing and applying suitable and beneficial substances to the user's skin.

Preferably, the plurality of fibres extends in the application position from the base layer towards the user's skin. The plurality of fibres may comprise a proximate end fixed to the base layer and a free distal end preferably adapted to be in contact with a user. Preferably, the plurality of fibres extends at an angle α of about 60°-120°, more preferably of about 75°-105°, and most preferably of about 90° from the base layer (in cases of doubt, preferably, from the tangent to the base layer). In other configurations the preferred angle may be about 45°. These angles refer to the unworn or unused state of the cushion while it will be understood that the orientation of the fibres may change when contacting or being pressed against a user's face. The plurality of fibres may be arranged substantially parallel to each other. The orientation of the plurality of fibres may also change in different regions of the interface or base surface. Alternatively or additionally, the fibres may be arranged at a density between about 10 to 100 $g/m^2$, preferably between about 20 and 65 $g/m^2$, and most preferably between about 30 and 45 $g/m^2$. The fibers may also be randomly oriented. Fibers may be made of viscose and/or polyamide. Viscose fibres may be arranged between about 10 and 50 $g/m^2$, more preferably between about 20 and 40 $g/m^2$, and most preferably between about 25 and 35 $g/m^2$. Polyamide fibres may be arranged at a density between about 25 and 65 $g/m^2$, more preferably between about 35 and 55 $g/m^2$, and most preferably between about 40 and 50 $g/m^2$. Alternatively or additionally, preferably, the fibre(s) has/have a length or height measured from the proximate end to the distal end of between about 0.01 and 5.0 mm, more preferably between about 0.05 and 2.0 mm and most preferably between about 0.1 and 1.0 mm. The fibre(s) may have a substantially round cross sectional shape. Alternatively or additionally, the fibre(s) may have a titre (yarn count) value [dtex] in a range of about 0.01 to 10 dtex, more preferably about 0.1 to 5 dtex, most preferably of about 0.5 to 2 dtex, wherein the Dtex is measured in g/10,000 m. The fibre(s) may be adapted to collapse, preferably in the application position and thus, when being pressed against a user's face. Preferably, the fibres simply bend away or buckle, rather than be compressed. The fibre(s) may predominantly tilt and/or bulge.

The fiber(s) may provide an adapted or controllable softness or resilience. Moreover, the sealing and/or ventilation as well as the sliding resistance may be adaptable/controllable by the variation of the above parameters of the fiber(s). By selecting the length, density, diameter, material and/or arrangement of the fiber(s), such as the orientation of the fiber(s), the properties of the seal forming portion may be adapted to a particular need. For instance, an open cell foam material may be provided with a seal forming portion providing airtight properties to the open cell foam which may reduce the risk of unintended leakage. The seal forming portion may be of a seal forming structure. The seal forming portion may form a perimeter arranged to surround an entrance to the airways of the patient so as to facilitate the supply of air at positive pressure to the airways. The patient interface preferably sealingly contacts a user's face. However a defined, diffused leakage at the seal forming portion located around the entire perimeter may amount to between 2 l/min and 60 l/min, preferably between about 5 l/min to 30 l/min.

The seal forming structure may form an opening for receiving a patient's nose and/or mouth. Preferably, it forms at least a portion of and preferably the whole perimeter of such an opening. The seal forming portion is preferably essentially triangularly shaped. The seal forming structure may contact the user's face around nose ridge (nasal bone, lateral cartilage, septum cartilage) and the lip superior or lip inferior. The seal forming structure may have other alternative configurations such as a nasal pillow configuration with a shape adapted to cover the nostrils.

The fibers may have a varying resilience along the perimeter of the seal forming portion. In particular, the fibers may provide in the application position a higher resilience in the nose bridge area than in other areas of the seal forming portion.

The fibers may be affixed to the base surface by an adhesive, which may form the intermediate layer. Any suitable bio-compatible adhesive may be used. For instance, the adhesive may be coated on the base surface. Alternatively or additionally, the base layer material itself may be adapted to hold or fix the fibers. The seal forming portion may be made of or may comprise a resilient material, preferably adaptable to the contour of a user's face. For instance the resilient material may provide the base layer. In this configuration not only the fibers but also the material of the seal forming portion improves the adaptability of the patient interface since not only the fibers provide resilience but also the material of the portion to which the fibers are fixed.

The seal forming structure may be made of or comprise a foamed or foam material, preferably as the base layer. The foamed material may provide an additional resilience. As outlined above, in addition to serving as a reservoir for substances, air tightness of the seal forming portion may be improved by applying the seal forming portion on open cell foam. The seal forming portion may be made of or comprise a textile material, preferably a resilient textile, preferably as the fibre layer. Besides foam and textile materials also other bio compatible materials may be used as the base layer material of the surface to which the fibres are fixed as long as the material provides appropriate mechanical properties comparable to those of a foam or textile material and as long as the fibres may be fixed to the material. Preferably, the fibres are synthetic fibers, preferably made of at least one of the group: cotton, wool, viscose, nylon, or cellulose. However, any natural or synthetic fiber may be used as long as it is bio-compatible, has comparable mechanical properties as the afore-mentioned materials, and can be applied in a suitable length. The fibers may be stitched, flocked, adhered and/or woven to the base surface.

With the seal forming structure according to the present technology, not only the seal forming surface properties in contact with a patient may be influenced in order to increase the wearing comfort but also the properties of the base material or base surface to which the fibers are fixed may be influenced in a positive manner. Also, the defined provision of a substance to the user may beneficially be achieved. At least a portion of the fibers may be provided in tufts, preferably of similar length. The fibers of a tuft may be twisted. Moreover, the fibers may be looped or cut at the second end. The fibers may be provided in a multi-level arrangement. Preferably, a first portion of the fibers is provided with a first length establishing a first level of second ends. Moreover, a second portion of the fibers may be provided with a second length establishing a second level of second ends. The multi-level arrangement may further improve the resilience behavior of the seal forming portion. This may affect comfort of use and/or the leakage or sealing behavior of the patient interface.

The seal forming structure may be provided on a flexibly resilient cushion, pad, sealing lip and/or membrane of a patient interface. The fibers may be made of a material which contributes in guidance of a substance from the base layer to the user's face, e.g. by serving as a 'wick', and/or which comprises a substance to be released to the skin of a user or patient. Preferred substance releasing materials are known from the application WO 2012/131001 the content of which is incorporated by reference. The fibers may be in fluid communication with a material, preferably the base layer, adapted to release substances which may be transported by the fibers to the skin of a user or patient. Such material may additionally or alternatively be contained in the patient interface, e.g. in a void or hollow contained therein, e.g., in the resilient cushion, pad, sealing lip and/or membrane of the patient interface.

As indicated above, the fibers of the fibre layer preferably serve as a "wick" to enable the substance to migrate from the base layer to the patient's skin. This may be achieved by one or more physical effects, such as migration, concentration differences, capillary forces, pressure differences, membrane effects etc. Besides, the 'volume' of the fibre layer, i.e. the spaces between the fibres may, alternatively to the base layer or in addition thereto, serve as a kind of reservoir or sponge which holds a substance. According to a preferred aspect of the present technology, the base layer serves as a kind of 'reservoir' for a substance while the fibre layer serves as some kind of 'buffer' for the already released substance.

According to a preferred aspect of the present technology, the pad is adapted to contain and/or comprises a substance contained in the fibre layer and/or the base layer.

The substance may preferably be absorbed by, reside in and/or be released from the base layer. Preferred substances may take the form of an oil, a low-viscosity gel, a liquid or a powder. In case of a powderous substance, it is preferred that the substance resides upon the pad's surface and/or within the fiber layer. In case of an oil based or gel-like or liquid substance, it is preferred for the substance to soak into and releasably reside in the fiber layer and/or the foam base layer, which then serve as a reservoir for the substance According to preferred aspects of the present technology, the substance has a therapeutic and/or cosmetic effect, and/or improves the seal and/or comfort of the patient interface, preferably of the cushion and/or the forehead support. Such substance may be commercially available, customized or specially developed.

One physical characteristic of the substance which may be chosen or adapted to optimize the pad for use with a given substance and/or a substance for use with a given pad is the viscosity. The viscosity is preferably characterized as dynamic viscosity.

It is desirable for the viscosity to be balanced against other material properties such as above described porosity or permeability of the base layer and/or the intermediate layer, to achieve a desired, preferably near-constant, release rate of the substance from the base layer to the fibre layer and thus the user.

For example, a (e.g. gel-based) substance of comparatively low viscosity may require smaller pore sizes than a (e.g., oil-based) substance of comparatively high viscosity to achieve the same or about the same desired flow rate.

Preferred values (at 20° C. ambient temperature) of such viscosity may be from about 1.0 mPa*s to about 104 mPa*s, preferably from about 5 mPa*s to about 100 mPa*s, and further preferred from about 10 to about 100 mPa*s, particularly for oil-based substances.

In addition or alternatively, preferred values (at 20° C. ambient temperature) of such viscosity may be from about 0.5 mPa*s to about $11^3$ mPa*s, preferably from about 2.5 mPa*s to about 80 mPa*s, and further preferred from about 5 to about 50 mPa*s, particularly, for gel-based substances.

A physical characteristic of the pad according to the present technology together with a given substance or kind of substance may be the flow rate or substance release rate at which the substance contained in the base layer is released to the fibre layer and thus a user's skin.

Such rate of substance flow may be dependent on various influencing factors. Amongst these may be the (above described) porosity/permeability of the intermediate layer and/or the base layer and/or the viscosity of the substance. Another or additional factor might be the force by which the sealing is created, e.g. by tightening the headgear straps, would have an influence as it affects the reservoir's internal pressure. In view of the fact that, for example depending on the size and geometry of the pad (e.g. for a nose and mouth mask, a nasals mask, nasal prongs and/or size of the patient) the overall contact surface between pad and patient may vary. Therefore, base on the findings underlying the present technology, preferred release rates are defined as per $mm^2$.

The preferred flow or substance release rate may also depend on the specific nature of the substance and the required amount of substance per time and facial area as well as, e.g., on the speed at which the substance can be absorbed by the user's skin.

Also, the release rate may depend on the actual application in terms of, e.g., whether it is a single-use application for one use, or a multi-use application for a number of subsequent usages. A single use application may be designed to release the substance contained in the base layer reservoir over a predefined time, for example one night (e.g. 8 hours) or one week (7*8 hours). For multi-uses applications, it may be desirable, for a given amount of substance contained in the base layer reservoir, to provide a reduced flow rate, e.g.

the single-use flow rate divided by the number of envisaged uses. In addition or alternatively, the reservoir may be increased in size accordingly. In here, preferred values are given for a single-use (i.e. one night) application. The desired flow rate may thus depend on the desired usage period before disposal or re-fill; e.g., a pad designed to be disposed after one night may have a higher flow rate than one designed to be used for several nights in a row; or, a pad designed to be used for several nights in a row may require a larger reservoir to contain a sufficient amount of substance.

A preferred release rate per $mm^2$ of contact surface has been found to be, particularly for single-use application, between about 0.01 mg/hr and about 10 mg/hr, preferably between about 0.5 mg/hr and about 5 mg/hr, and also preferred of about 0.1 mg/h, min.

Preferred substances for use with the present technology have an objective and/or subjective beneficial effect to the wearer or the therapeutic effect of the administration of breathable gas at elevated pressure and thus may improve patient compliance. Preferred exemplary substances, their effective content and potential advantageous effects may be taken from the non-exhaustive lists according to table 1 (substance classification) or table 2 (sample substances). As can be taken from the columns 'effects' in these tables, preferred substances may have beneficial therapeutic and/or cosmetic effects, and/or improve the seal and/or comfort of the patient interface. Amongst these effects are, for example, soothing, cooling, vitalization, moisturizing, anti-inflammation, smoothening, anti-aging, odor, improvement of collagen synthesis, increased hyaluron production, wrinkle reduction, vitamin C replacement, anti-oxidation, skin regeneration, reduction or skin irritations, purification, and many more. As will be readily noted, preferred substances are of kinds readily known and available in the art, as also apparent from tables 1 and 2. The above discussed parameters of the pad, particularly of base layer, intermediate layer and/or fibre layer may be chosen and/or adapted to be most suitable for use with one or more of such substances.

With reference to table 2, a sample pad has been tested on various testers with different substances. The sample pad was made of a flocked cosmetic PU foam C32NR as laid down in data sheet for foams C32RT and C32NR (December 12) of Koschaum GmbH, Abenberg, Germany.

As can be taken from the test results, the pad according to the present technology allows multiple existing substances to be advantageously used therewith. It will be appreciated that some of the substances considered unsuitable might still be suitably used with a pad having adapted parameters, as indicated above. However, as regards general wearing comfort and improved micro-adjustability, the chosen parameters of the pad are of general advantage. Thus, the acceptable substances according to table 2 along with the test pad, potentially varying within the preferred pad features as discussed herein, are of particular advantage.

As has been found out, a pad according to the present technology allows advantageous use and application of a variety of substances leading to the advantages as outlined above and as specified, e.g., in tables 1 and 2.

Amongst particularly suitable substances, there are liquid and gel like substances with low to very low viscosity, substances with powder like consistency and substances with oily consistency (low viscosity).

Liquid and gel like substances with low to very low viscosity:

If the substance's viscosity is sufficiently low, e.g., in the order of a low to very low viscosity gel or a liquid, it can well soak into the fibre layer, particularly comprising cotton fibers, and/or the underlying base layer, preferably a foam pad. Generally, the lower end of the above specified viscosity range may be beneficial for a quick absorption of the substance into the pad, i.e. the "loading" of the pad.

It has been found that the substance can well be contained or reside in the fibre layer, and even better in the base or foam layer, particularly without evaporating immediately. Retention times of several days have been observed in the trial.

According to a preferred advantageous aspect of the present technology, particularly to protect and/or to further reduce evaporation, the pad including a substance applied thereto or contained therein may be provided with a protective cover and/or air tight wrapping. Such cover or wrapping may be removed by the user before use. It will be appreciated that this aspect is not limited to liquid and gel like substances with low to very low viscosity but may be applied with any substance or even to pads not containing any substance.

Powder Like Consistency:

Further preferred, a powder may reside within the, preferably cotton, fiber layer without actually permeating into the underlying base, preferably foam, layer. Upon contact to user's skin, a combination of skin moisture and/or small movements of the pad against the skin have been found to cause the powder or powder like substance to rub off onto the skin, and/or to adhere to the skin, assumedly by skin moisture.

Again, a protective cover and/or air tight wrapping may be applied here too, particularly to prevent powder from coming off during transport or clogging due to (ambient) air moisture.

Oily Consistency (Low Viscosity):

If a substance's viscosity is sufficiently low, e.g. in an oil, it can soak into the, preferably cotton, fibres of the fibre layer and/or the underlying base, preferably foam, pad.

It has been found that the substance can well reside in the fibre layer, and even better in the base (foam) layer, particularly without evaporating immediately. Retention times of several days have been observed in the trial. It is notable that an oil based substance is less prone to evaporation than a gel based substance. Therefore it is assumed that a less complete sealing, e.g. "only" a protective cover rather than an air tight wrapping, may be sufficient to protect the pad including such substance prior to use.

Other substances have been found generally unsuitable in the trial. Amongst those are gel like substances with medium to high viscosity and substances with cream or pasteous consistency. The term "unsuitable" particularly includes reference to the lack of the ability of the substance to be loaded into the present pad via gravity, e.g., by dripping the substance onto the pad. However, by loading under pressure, e.g., with a syringe and a suitably large pore size, such substances may still be rendered suitable, as suggested above and as also applicable for the below discussion.

For example, it has been found out that for gel like substances with medium to high viscosity, e.g. if a substance's viscosity is too high, it may not easily soak into the foam base layer. Rather, a larger amount of such substance will reside on the pad's surface, prone to being rubbed off prematurely and also reducing the overall amount of substance that can be applied to a pad. It has further been found that the lower water content makes the substance more prone to evaporation.

Moreover, it has been observed that cream or pasteous substances may not permeate into the base foam layer at all, and thus may reside entirely upon the surface and in the (cotton) fibre layer. This may cause the (cotton) fibers to clog, causing an unsightly appearance and also reducing the comfort perception on the user's skin.

Finally, a number of substance ingredients has been found to be of particular advantage, such as pleasant odours, skin care substance or substances improving, e.g., CPAP therapy.

Amongst suitable active ingredient of substance are those exhibiting a pleasant odour. If such substances are used, the pad may emit an odour, e.g. as in an aftershave or in a perfume, making it more pleasant to wear for patients and/or bed partners. Similarly, various skin care substances may be applied to improve one or more of: skin health, skin moisture content, reduce inflammation, soothing effect, support collagen synthesis, smoothness, anti-aging, vitamin supply, anti-oxidizers, lipid regulation, cooling perception, improved regeneration. Alternatively or in addition, substance improving CPAP therapy may be used. These may be any substances improving patient comfort in whatsoever way, thereby improving therapy compliance. Also, for example, substances may be applied having no therapeutic effect in itself, but having a beneficial effect on CPAP therapy by ameliorating the therapies undesired side effects. This may be achieved, for example, either by means of an oily or gel-like substance that may reduce friction between skin and pad, thus the patient interface, thereby effectively reducing the occurrence of sore spots on the face, and/or by means of a substance that has a certain extent of sticky or adhesive effect, e.g., achieved through a high viscosity gel or adhesive, so that the pad's and thus the interface's sealing performance is improved.

Other substance ingredients have been found rather unsuitable for use with the present technology. Amongst those are, for example, solvent containing substances, substances that decay over time, or substances that require special storage conditions.

For example, where a substance contains solvents, e.g., as in certain types of aftershaves, the solvent may cause the intermediate layer, e.g. an adhesive layer, between (cotton) fiber layer and the base (foam) layer to be temporarily softened. This may lead to the cotton fibers bending/falling/tilting/sinking into the adhesive before it solidifies again. This has been observed to cause the fibers to lose their upright orientation, leading to clogging and unsightly appearance and reduced comfort when touching the skin. The exact nature of unsuitable solvents is dependent on the actual material (or adhesive) used to bond the cotton fiber layer to the foam base material.

Other substances may be prone to decay over time when applied to the pad. This has been observed, e.g., in certain natural extracts based on fish oils or algae, which decayed after short storage intervals, e.g., emitting an unpleasant odour.

Substances that require special storage conditions, such as, e.g., a continuous cooling chain, would also be considered generally unsuitable. However, will be apparent, no such substance was used in the trial discussed herein.

As regards the way a substance is applied to a pad according to the present technology, different ways and means are feasible. For example, the substance may be pre-applied at the manufacturer's end. The manufacturer may thus produce the pads with a substance applied to them, preferably protected pad and substance during transport and storage by a protective cover and/or (partly) air tight protective wrapping. As discussed above, the pad may be suitable for use only for a short duration of time (a few nights) until the substance reservoir is depleted. Alternatively, it may be refilled as discussed below.

In addition or alternatively, the manufacturer may supply a number of pads along with dosing equipment containing the substance. Patients may then apply it by themselves just before use or after the pre-applied substance has been used. This will enable much easier shipment and production process. However, such home refill by the patient will bear the risk of user errors (e.g. too much or not enough substance used); however, this may be prevented by appropriately designed dosage or refill means along with suitable instructions.

Further in addition or alternatively, the pad may be predisposed to accept a substance "from the patient's bathroom closet". The Manufacturer may provide guidelines as to which substance can be used as well as some sort of dosing or refill equipment.

Further in addition or alternatively, the pad may be activated upon contact to air or moisture. For example, a substance may be applied to the pad, and the pad may subsequently be enclosed in an air-tight wrapping. The substance may be predisposed such that it activates once the seal is broken and it comes into contact with air and/or moisture. This may be particularly beneficial for transport and storage. However, it may also bear limitations regarding the range of substances that can be used.

Along with the preferred pad according to the present technology, there may be different preferred means or ways of releasing a substance from the pad. One of these is skin moisture, which is particularly applicable to powderous substances. The powder applied to the (cotton) fibre layer may adhere to the patient's skin due to natural skin moisture, so that it's active substances can be released to the patient's skin. It is proposed to chose the parameters such that that the affinity of the powder to skin is higher than its affinity to dry (cotton) fibers of the fibre layer, particularly due to skin moisture.

Another preferred effect of release is friction. Small movements of the pad against the user's skin during use, e.g. resulting from breathing gas pressure swings and/or face movements, may cause the substance to "rub off" onto the user's skin.

In addition or alternatively, contact/diffusion principles may be applied. As the pad containing the substance is applied to the patient's face, the skin will begin to absorb the substance contained in the pad through the usual mechanisms (such as diffusion) as would also apply to known cosmetic substances, until the reservoir in the pad is depleted.

In addition or alternatively, forces applied to the cotton pad, e.g. resulting from therapy pressure swings or headgear tension force, may slightly compress the cotton pad. This may lead to a volume reduction of the substance reservoir in the (cotton) fibre layer and/or (foam) base layer, going along with a pressure increase, so that substance is squeezed from the pad and released onto the patient's skin.

In addition or alternatively, the effect of evaporation may apply, predominantly to, e.g., odours. E.g., a solvent based substance may evaporate into the air, from where it is sensed by the patient and/or bed partner.

In order to allow the substance contained in the base layer acting as a reservoir to be released in a controlled manner via the intermediate layer acting as a membrane to the fibre layer for contacting the face of a user, it is preferred that the base layer is sealed along its remaining surface, i.e. the surface not being in contact with or acting as the intermediate layer. This may be achieved by sealingly adhering the base layer to an underlying structure, such as a cushion, or sealing the outer surface of the base layer by providing a (separately applied or integrally formed) sealing layer or skin. For example, the base layer could be formed with a skinned—and preferably substance tight—outer surface. Such skin could partly be removed and replaced by the intermediate layer or worked, e.g. by introducing pores as defined above, to partly become the intermediate layer. The (thicker) adhesive layer in the above addressed samples forms a barrier towards the mask side, the rounded edge manufacturing process encloses the reservoir. Alternatively, applying an impermeable intermediate layer to the mask side and joining it to the permeable layer on the patient side would work. Alternatively, the pad can be foamed into a mould rather than die-cut from a sheet. In this case, it would form a closed skin where it contacts the mould.

This preferably prevents the substance contained in the base layer from being released from the base layer along any other way than in the defined manner via the intermediate layer.

As indicated above, the pad preferably exhibits a ring-like, closed geometry, particularly when being used as a seal forming structure around, e.g., a users nares, nose and/or mouth. Alternatively, and as will be readily noted, e.g. when being for use as a support pad, e.g. in use with a forehead support of a patient interface or the like, the pad may have other shapes or geometries, such as oval, circular and/or strip like.

As further indicated above, the pad according to the present technology is contained in a package, the package preferably being air tight. This is of particular advantage when the substance is applied at the manufacturer's site but also if the pad is sold and delivered free of substance but shall be kept clean and sterile before use and potential application of the substance at the patient's site.

According to a preferred aspect of the preset technology, a set of pads each having applied the same or different substances, as discussed above, may be provided and sold along with a patient interface or separately. This may have the advantage of providing a 'stock' of pads to the patient who, upon having used one pad such that the substance initially contained therein is used off, may exchange it with a fresh pad filled with substance. In addition or alternatively, this allows patients to use different pads loaded with different substances in a sequence. This sequence or order of substances may be chosen so as to be of particular advantage and benefit of the patient.

Summarizing a preferred aspect of the present technology, a patient interface system (e.g., as referred to above) may be provided with a thin foam pad flocked with cotton fibres. This pad, forming the interfaces seal forming structure, may be applied to a, preferably LSR (Liquid Silicone Rubber) under-cushion by means of an adhesive, so that the cotton pad itself is user-replaceable. The, preferably bellowed, LSR, under-cushion is responsible for makro-adjustment to the patient's facial physiognomy (large scale) while the cotton pad component forms the micro-adjustment part (small scale).

The pad is loaded with a substance, either pre-loaded by the manufacturer or by the patient himself prior to using the pad. Said substance, as discussed above, is released to the patient's skin during use at a preferably predefined rate and provides subjective and/or objective beneficial effects to the patient. If preloaded, the cotton pad will have a protective cover layer or an air-tight wrapping or sealing to ensure the substance does not degrade during transport and storage. In case of application by patient, a dosing equipment may be provided to assist the patient in loading a substance to the pad. Such equipment may be a syringe or a specifically designed tool. The pad may be predisposed to accept a range of "approved products" "from the patient's wardrobe".

According to the present technology, the pad loaded with substance is intended to work in either or a combination of the following ways:

The substance applied to the cotton pad may reduce the friction between mask cushion (i.e. here the pad) and face skin, thereby leading to a reduction of pressure marks or skin reddening. The substance applied to the cotton pad may be sticky (either highly viscous or by means of an adhesive) so that the seal between cotton pad and face skin is improved. The substance may have a therapeutic or cosmetic effect (as discussed in more detail above). The substance may emit a pleasant odour to make wearing the mask more desirable. This may lead to an increase in patient comfort, patient health and ameliorate potential downsides of NIPPY therapy, thus increasing therapy compliance.

The pad according to the present technology relates to a pad for a patient interface. As discussed above, the pad may comprise a resilient material layer with a seal forming portion for sealingly contacting a user's skin. The pad may comprise a seal forming portion as described above. However, the present pad may be provided with any other seal forming portion as well.

The pad may be adapted to be releasably connected to a resilient cushion. The pad may be configured as a detachable pad or may be integrally formed with the cushion. The cushion may be any kind of cushion as long as it is contoured and/or pre-shaped to approximate and/or match the contours of a user's face. The cushion may be made of an elastomeric material, for instance a silicone such as liquid silicone rubber (LSR), compression mold silicone rubber (CMSR) and/or thermoplastic elastomers (TPE) or other elastic materials.

The pad may be configured to be a disposable pad. For instance, the pad may be disposed after a certain usage. Moreover, pads of different sizes and/or with different wearing properties (e.g. softness, substance releasing, sweat transport, . . . ) may be adapted to be connected to the same cushion of a patient interface. The user may try pads with different shapes, different resilience, different tactile impressions, different substances and/or different structures together with the same cushion. That is, the pads may allow for a quick and cost-effective adaption of the patient interface to the user's needs. This may even be effected spontaneously without the need to see the retail seller or even a physician. Moreover, the pad may be tailor-made to the individual shape of the user in a cost effective way since the basic shape may be relatively simple. In principle any suitable resilient material can be used for the pad/contact surface.

The pad may be provided with a cushion contacting portion adapted to be connected with the cushion. The pad may be fixed to the cushion and the cushion contacting portion by appropriate means such as Velcro or adhesive applied to the cushion and/or pad. Alternatively, double-sided adhesive tape may be used for connecting the pad to a cushion.

The cushion contacting portion and/or the pad may have a width of at least 5 mm, preferably of at least 8 mm, and most preferably 10 mm or more. The width of the cushion contacting portion may vary around the perimeter of the face contacting contour, e.g. be narrower at the nose than at the cheeks or chin. The pad may protrude beyond the shape of the cushion, e.g., the flange portion of the cushion for at least several millimeters, preferably about 1.5 to 10.0 mm, most preferably 3.0 to 5.0 mm, preferably on each side. The pad may be provided with a sufficient width to ensure that during use only the pad and not the cushion contacts the user's face. This protrusion may be present both along the outer perimeter as well as along the inner perimeter of the pad-contacting portion of the cushion. The protrusion may also vary along the contour, e.g., a different protrusion may be provided at the nose area than at the cheeks or chin area. The cushion contacting portion may be substantially parallel to the seal forming portion of the pad. Preferably, the cushion contacting portion is located on a side opposite of the seal forming portion. The cushion contacting portion may be substantially flat and/or planar. The pad may be provided with a pad thickness between about 0.5 to 26 mm, preferably between about 1.0 to 13 mm, more preferably between about 2 and 10 mm, and most preferably between 4 and 8 mm According to a preferred example, the pad has a thickness of about 6 mm Such pad may be made of any of the herein discussed materials. A pad of too high thickness may hinder the contribution of the underlying cushion support structure, preferably the, e.g., I- or T-beam structure as discussed in EP 14 17 2818.8 and U.S. Ser. No. 14/741,930, which are incorporated herein by reference. A too thin pad may be less comfortable to the patients and/or also negatively influence the micro adaptation to the patient's face. The pad may be made of a foam material with a thickness between about 1.5 to 26 mm, preferably between about 3.0 and 13 mm E g an open cell foam may be provided with a thickness in the range of about 3.0 to 7.0 mm A more rigid closed cell foam, e.g., may be provided with a thickness between about 7.0 and 13.0 mm A fabric layer may have a thickness between about 0.5 to 6 mm, preferably between about 1.0 and 3.0 mm. The pad thickness may vary along the perimeter of the pad. Moreover, the pad thickness may vary in a direction perpendicular to the direction of extension along the perimeter. The average thickness of the pad may vary between about +/−75%, preferably between about +/−50% of the average thickness of the pad measured in the direction C. The seal forming portion may be curved in a cross-sectional view (i.e. in a view perpendicular to the extension of the pad along the perimeter; cf. FIG. 8a, 8b of EP 14 17 2818.8 and U.S. Ser. No. 14/741,930, which are incorporated herein by reference). The pad may thus have, in a cross-sectional view, an at least two-dimensional shape. The shape of such a pad may also be called a 2.5D shape. The pad may be a substantially flat material with a bulge or a curve in the patient contacting portion. Such a pad may be easy to manufacture by punching or cutting out of a sheet material as further described below. The thickness of the pad, as referred to above, is preferably substantially thinner than the thickness of an underlying cushion structure, as discussed further herein. Such thickness may be seen in direction towards a patient's face. Preferably, the thickness of the pad is less than 70% of the cushion's thickness, more preferably, the pad's thickness is less than 50% of the cushion's thickness and more preferably, the pad's thickness is less than about 30% of the cushion's thickness.

The pad may be provided with a higher resilience than the resilience of the cushion to which the pad may be attached. The cushion may be provided with an, preferably elastic, resilience to generally adapt to the individual shape of a user's face. That is, the cushion may be adapted to provide a macro-adaption to the individual shape of a user's face. The pad may be adapted to provide an additional (micro-) adaption to the individual shape of a user's face. With other words, the patient interface may comprise a cushion providing a first resilience and a, preferably releasable, pad providing a second resilience, the second resilience being higher than the first resilience.

In conventional masks, the sealing effect is achieved by applying a locally relatively high sealing force onto the face of the patient, because the functions of macro- and micro-adaptation are both realized in one cushion and often by the same material or coupled by fully enclosing or embedding one material in another one. These functions are decoupled in the present technology. The cushion may allow for an (elastic macro-) adaptation to the shape of the patient's face. The macro-adaptation may primarily be a function of the cushion (e.g. below description of the T-shape as one preferred embodiment). The cushion may be adapted for an elastic deformation. I.e., the cushion may deform during use and may substantially return to its original shape. The pad may allow for a very fine adaptation to the face of the patient (micro-adaptation). The pad may distribute the sealing forces to a larger area in the face of the patient. Moreover, because of an improved micro-adaptation of the pad, the overall sealing force that is required may be lower while securely avoiding undesired leakages. As a result, the present technology may increase the wearing comfort for the patient. The patient interface may adapt itself to various individual contours of many different patients. The fit of the patient interface perceived by the patient may be improved. At the same time, the required number of different sizes and shapes of cushions and mask shells may be reduced. Because of the material/surface properties and due to the improved force distribution of the pad, the wearing comfort of the mask may be improved as compared to existing systems.

The pad may comprise a foam material, preferably an open-cell foam. Preferably, the foam material is a polyurethane foam. Also other bio-compatible foams may be used. The pad may comprise at least a portion which is at least partly filled with a substance as discussed above. The substance may, in particular, be a liquid or a gas, preferably a gel material, air, water or oil. The pad may comprise a textile material or a combination of a textile material and a foam material. The textile material may be back molded with a foam material (foam applied to the rear side of the textile). The pad may be made of a textile material back molded with a polyurethane foam. Any polyurethanester or polyurethaneter foam may be used. For instance, medical polyurethane foam may be used which may be provided with an additional foam layer. Such foams with additionally applied foam layers could be configured as such foams used in wound dressings, i.e. to enhance wound healing. Textured fabrics may improve air circulation and may stimulate the tissue. Textured foam materials (foam material with texturing; neoprene and/or textile-coated neoprene) may be used. The pad may comprise a gel which forms a skin as well as gel enclosed in a film. The pad may comprise an adhesive material, and preferably an adhesive gel. The adhesive may be adapted to securely hold a patient interface in the application position. That is the adhesive may be adapted to fix the patient interface thereby replacing a headband means. By using such adhesive materials headbands may no longer be necessary. The entire seal forming portion being in contact with a user's face may be provided at the pad. The shape of the pad viewed from the face contacting side C may substantially correspond to the shape of the pad contacting portion of a cushion.

The pad, preferably the seal forming portion, may form at least a portion of, preferably the whole, perimeter of an air supply opening. The pad is, in a top view, preferably essentially triangularly shaped, preferably with round corners. The pad may contact the user's face around nose ridge (nasal bone, lateral cartilage, septum cartilage) and the lip superior or lip inferior. The pad may have other alternative configurations such as a nasal pillow configuration with a shape adapted to cover the nostrils. The pad may essentially follow the common shape of the cushion and/or patient interface (full-surface mask, nasal mask or nose cushion mask), e.g. may contact the face of the patient over the entire circumference or perimeter. However, it is also possible to apply the pad only in selected areas of the patient interface so that, e.g., sensitive areas of the face are particularly relieved. In this case, the sealing function in the remaining part of the face may be achieved by a single- or double-wall cushion in accordance with the prior art.

The pad may only provide a portion of the entire seal forming portion. At least a portion of the cushion may be single or double walled. Preferably, the cushion comprises a seal-forming portion in locations where no pad is applied. Preferably, a single- or double-walled cushion structure is applied in the area of the nose ridge. The single or double walled structure may be configured as membrane.

4.2.2 Plenum Chamber

The plenum chamber 3200 has a perimeter 3210 that is shaped to be complementary to the surface contour of the face of an average person in the region where a seal will form in use. In use, a marginal edge 3220 of the plenum chamber 3200 is positioned in close proximity to an adjacent surface of the face. Actual contact with the face is provided by the seal-forming structure 3100. The seal-forming structure 3100 may extend in use about the entire perimeter 3210 of the plenum chamber 3200.

4.2.3 Positioning and Stabilising Structure 3300

The seal-forming portion 3100 of the patient interface 3000 of the present technology may be held in sealing position in use by the positioning and stabilising structure 3300.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a cushion into sealing contact with a portion of a patient's face. In an example the strap may be configured as a tie.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

4.2.4 Vent

In one form, the patient interface 3000 includes a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure 3500, e.g., a swivel 3510.

4.2.5 Decoupling Structure(s)

In one form the patient interface 3000 includes at least one decoupling structure 3500, for example, a swivel 3510 or a ball and socket 3520.

4.2.6 Connection Port

Connection port 3600 allows for connection to the air circuit 4170.

4.2.7 Forehead Support

In one form, the patient interface 3000 includes a forehead support 3700.

4.2.8 Anti-Asphyxia Valve

In one form, the patient interface 3000 includes an anti-asphyxia valve 3800.

4.2.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

GLOSSARY

For the purposes of the present technology disclosure, in certain forms of the present technology, one or more of the following definitions may apply. In other forms of the present technology, alternative definitions may apply.

4.2.10 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Continuous Positive Airway Pressure (CPAP) therapy: CPAP therapy will be taken to mean the application of a supply of air to an entrance to the airways at a pressure that is continuously positive with respect to atmosphere. The pressure may be approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

4.2.11 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240

Polycarbonate: a typically transparent thermoplastic polymer of Bisphenol-A Carbonate.

4.2.12 Aspects of a Patient Interface

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or a rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Plenum chamber: a mask plenum chamber will be taken to mean a portion of a patient interface having walls enclosing a volume of space, the volume having air therein pressurised above atmospheric pressure in use. A shell may form part of the walls of a mask plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Vent: (noun) the structure that allows an intentional flow of air from an interior of the mask, or conduit to ambient air, e.g. to allow washout of exhaled gases.

4.2.13 Terms Used in Relation to Patient Interface

Curvature (of a surface): A region of a surface having a saddle shape, which curves up in one direction and curves down in a different direction, will be said to have a negative curvature. A region of a surface having a dome shape, which curves the same way in two principal directions, will be said to have a positive curvature. A flat surface will be taken to have zero curvature.

Floppy: A quality of a material, structure or composite that is one or more of:

Readily conforming to finger pressure.

Unable to retain its shape when caused to support its own weight.

Not rigid.

Able to be stretched or bent elastically with little effort.

The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during respiratory pressure therapy.

4.3 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

The invention claimed is:

1. A pad for forming a seal forming structure against a user's skin for use with a patient interface, the pad comprising:
    a base layer having a first permeability to at least one substance;
    a fiber layer comprising a plurality of fibers for contacting a patient's skin, each fiber of the fiber layer being spaced apart from the base layer; and
    a connection layer for connecting the fibers to the base layer, the connection layer having a second permeability to the at least one substance;
    wherein the base layer and/or the fiber layer is/are adapted to act as a reservoir for the at least one substance;
    wherein the first permeability is an adjusted permeability that is configured to allow controlled speed of substance migration from the base layer to the connection layer; wherein the second permeability is an adjusted permeability that is configured to allow controlled speed of substance migration from the connection layer to the fiber layer; and wherein the first permeability is greater than the second permeability.

2. The pad according to claim 1, wherein the connection layer allows a predefined/limited flow rate of the at least one substance therethrough.

3. The pad according to claim 2, wherein the predefined/limited flow rate is configured to be achieved as a result of contact with the patient's face.

4. The pad according to claim 1, wherein the connection layer comprises a micro-porosity, macro-porosity, and/or is adapted to allow diffusion at a chemical level.

5. The pad according claim 4, wherein the connection layer comprises the macro-porosity, and wherein the macro-porosity is configured to be mechanically created using a needle and/or a laser.

6. The pad according to claim 1, wherein the base layer has an average pore diameter ranging from about 0.2 mm to about 1.0 mm.

7. The pad according to claim 1, wherein the connection layer has a pore size ranging from about 0.5 mm to about 1.0 mm.

8. The pad according to claim 1, wherein the connection layer has a pore size ranging from about 0.1 µm to about 50 µm.

9. The pad according to claim 8, wherein the connection layer has a pore size of about 1 µm.

10. The pad according to claim 1, wherein the plurality of fibers are adapted to serve as a wick to enable the at least one substance to migrate from the base layer to the patient's skin.

11. The pad according to claim 1, wherein the connection layer is a mesh-reinforced layer.

12. The pad according to claim 1, wherein the connection layer is a foam.

13. The pad according to claim 1, wherein the connection layer is a membrane layer allowing the at least one substance to migrate (1) from the base layer, through the connection layer and to the fiber layer, and/or (2) from the fiber layer, through the connection layer, and to the base layer.

14. The pad according to claim 1, wherein the plurality of fibers are in fluid communication with the base layer.

15. The pad according to claim 1, wherein
    the base layer includes a first base surface and a second base surface opposite the first base surface;
    the connection layer includes a first connection surface and a second connection surface opposite the first connection surface, the first connection surface is directly coupled to the second base surface; and
    an adhesive layer includes a first adhesive surface configured to contact a cushion of the patient interface, and a second adhesive layer opposite the first adhesive surface and directly coupled to the first base surface.

16. The pad according to claim 15, wherein the adhesive layer includes a third permeability to the at least one substance that is less than the second permeability, the adhesive layer is configured to direct the substance toward the connection layer.

17. The pad according to claim 15, wherein the connection layer and the adhesive layer are joined by cold welding to create a rounded edge.

18. The pad according to claim 1, wherein the controlled speed of substance migration through the connection layer creates a pressure increase inside the base layer in response to a volume reduction as the base layer gets compressed.

19. The pad according to claim 1, wherein the second permeability is configured to allow for a substantially constant flow rate of the substance through the connection layer.

20. The pad according to claim 1, wherein a release rate per mm$^2$ of a contact surface of the fiber layer is between about 0.01 mg/hr and about 10 mg/hr.

21. The pad of claim 1, wherein the connection layer is a solid closed layer without pores on a macroscopic level, and includes pores on a microscopic and/or molecular level that allow permeability on a molecular level.

22. The pad of claim 21, wherein the pores on the microscopic and/or molecular level are a mesh or an interconnected molecular chain.

23. The pad of claim 1, further comprising pores randomly distributed throughout the connection layer and having random sizes, the pores configured to allow the substance to migrate between the base layer and the fiber layer.

24. A patient interface comprising a pad or set of pads according to claim 1 constituting a sealing structure, the patient interface further comprising,
   a positioning and stabilizing structure to maintain the pad or set of pads in sealing contact with an area surrounding an entrance to the patient's airways while maintaining a therapeutic pressure at the entrance to the patient's airways;
   a plenum chamber pressurized at a pressure above ambient pressure in use; and
   a gas washout vent configured to allow a flow of patient exhaled CO2 to an exterior of the patient interface to minimize rebreathing of exhaled CO2 by the patient.

25. The patient interface of claim 24, wherein
   the pad or set of pads is/are configured to compress while contacting the area surrounding an entrance to the patient's airways; and
   the second permeability is configured to allow for a substantially constant flow rate of the substance through the connection layer while the pad or set of pads is/are compressed.

* * * * *